(12) United States Patent
Pezzuto et al.

(10) Patent No.: US 7,414,042 B2
(45) Date of Patent: Aug. 19, 2008

(54) METHOD AND COMPOSITION FOR SELECTIVELY INHIBITING MELANOMA

(75) Inventors: John M. Pezzuto, River Forest, IL (US); Tapas K. DasGupta, River Forest, IL (US); Darrick S. H. L. Kim, Chicago, IL (US)

(73) Assignee: The Board of Trustees of The University of Illinois, Urbana, IL (US)

( * ) Notice: Subject to any disclaimer, the term of this patent is extended or adjusted under 35 U.S.C. 154(b) by 908 days.

(21) Appl. No.: 10/317,361

(22) Filed: Dec. 12, 2002

(65) Prior Publication Data

US 2003/0181429 A1    Sep. 25, 2003

Related U.S. Application Data

(60) Division of application No. 09/635,385, filed on Aug. 9, 2000, now Pat. No. 6,495,600, which is a division of application No. 09/189,698, filed on Nov. 10, 1998, now Pat. No. 6,225,353, which is a division of application No. 08/858,011, filed on May 16, 1997, now Pat. No. 5,869,535, which is a continuation-in-part of application No. 08/407,756, filed on Mar. 21, 1995, now Pat. No. 5,658,947.

(51) Int. Cl.
*A61K 31/56* (2006.01)
*A61K 31/15* (2006.01)
*A61K 31/19* (2006.01)
*A61K 31/196* (2006.01)

(52) U.S. Cl. .................. 514/169; 514/569; 514/640

(58) Field of Classification Search .................. 514/510, 514/554, 570, 573, 621, 640, 661, 703
See application file for complete search history.

(56) References Cited

U.S. PATENT DOCUMENTS

| 5,468,888 A | 11/1995 | Bouboutou et al. |
| 5,658,947 A | 8/1997 | DasGupta et al. |
| 2003/0153538 A1 | 8/2003 | Kuno et al. |

FOREIGN PATENT DOCUMENTS

| DE | 1 95 32 006 | 3/1997 |
| EP | 542622 | 5/1993 |
| WO | WO 94/26725 | 11/1994 |
| WO | WO 95/04526 | 2/1995 |
| WO | WO 96/29068 | 9/1996 |
| WO | WO 96/39033 | 12/1996 |
| WO | WO 00/46235 | 8/2000 |
| WO | WO 00/59492 | 10/2000 |
| WO | WO 02/09719 A1 | 2/2002 |

OTHER PUBLICATIONS

Pisha et al., Nature Medicine (1995), 1(10), 1046-51 (abstract).*
FASEB Journal, (1995) 9/8 (573).*
Batta et al., *Phytochemistry*, 12, 214-16 (1973).
Otsuka et al., *Chem. Pharm. Bull. (Tokyo)*, 29(11), (Nov. 1981).
Konoshima et al., *J. Nat. Prod.*, 1167-70 (1987).
Rajaram et al., *Indian Drugs*, 25, 211-12 (1988).
Maurya et al., *Fitoterapia, IX*, No. 5, pp. 468-469 (1989).
Patent Abstracts of Japan, vol. 013, No. 399, (Sep. 1989).
Yasukawa et al., *Oncology*, 48, pp. 72-76 (1991).
Ryu et al., *Archives of Pharm. Research (Seoul)*, 17(5), 375-377 (1994).
Fujioka et al., *J. Nat. Prod.*, 57, 243-7 (1994).
Yasukawa et al., *Phytomedicine*, 309-13 (1995).
Del Carmen et al., *Planta Medica*, 61/2, 182-185 (1995).
Kashiwada et al., *J. Med. Chem.*, 39, 1016-17 (1996).
Nagourney et al., *Proc. Annu. Meet. Am. Assoc. Cancer Res.*, 37:A2724 (1996).
Evers et al., *J. Med. Chem.*, 39, 1056-68 (1996).
Bogenrieder et al., *Proc. Annu. Meet. Am. Assoc. Cancer Res.*, 38:A1458 (1997).
Manez et al., *European Journal of Pharmacology*, vol. 334, No. 1, 103-105 (Sep. 1997).
Miles et al., *J. Pharm. Sci.*, 63(4), 613-15 (1974).
Miles et al., *J. Pharm. Sci.*, 65(2), 284-285 (1978).
Kingston et al., *J. Nat. Prod.*, 41(5), 499-500 (1978).
Kim et al., *Biorg. Med. Chem. Lett.*, 8(3), 1707-1712 (1998) (Abstract only).
Jeong et al., *Biorg. Med. Chem. Lett.*, 9(8), 1201-1204 (1999).

* cited by examiner

*Primary Examiner*—Phyllis G. Spivack
(74) *Attorney, Agent, or Firm*—Marshall, Gerstein & Borun LLP

(57) ABSTRACT

Compositions and methods are disclosed for treating melanoma wherein a betulinic acid derivative is the active compound in the composition to be administered. The compositions are optionally applied topically is inserted therefor.

19 Claims, 5 Drawing Sheets

METHOD AND COMPOSITION FOR SELECTIVELY INHIBITING MELANOMA

CROSS-REFERENCE TO RELATED APPLICATIONS

This application is a divisional of U.S. patent application Ser. No. 09/635,385, filed Aug. 9, 2000, now U.S. Pat. No. 6,495,600, which is a divisional of U.S. patent application Ser. No. 09/189,698, filed Nov. 10, 1998, now U.S. Pat. No. 6,225,353, which is a divisional of U.S. patent application Ser. No. 08/858,011, filed May 16, 1997, now U.S. Pat. No. 5,869,535, which is a continuation-in-part application of U.S. patent application Ser. No. 08/407,756, filed Mar. 21, 1995, now U.S. Pat. No. 5,658,947.

This invention was made with government support under U01 CA52956 awarded by the National Cancer Institute. The government has certain rights in the invention.

FIELD OF THE INVENTION

This invention relates to compositions and methods of selectively inhibiting tumors and, more particularly, to treating a malignant melanoma using plant-derived compounds and derivatives thereof.

BACKGROUND OF THE INVENTION

Over the past four decades the incidence of melanoma has been increasing at a higher rate than any other type of cancer. It is now theorized that one in 90 American Caucasians will develop malignant melanoma in their lifetime. While an increasing proportion of melanomas are diagnosed sufficiently early to respond to surgical treatment and achieve a greater than 90% ten-year survival rate, it is estimated that nearly 7,000 individuals suffering from metastatic melanoma will die in the United States this year.

For patients with metastatic melanoma not amenable to surgical extirpation, treatment options are limited. 5-(3,3-Dimethyl-1-triazenyl)-1-H-imidazole-4-carboxamide (dacarbazine, DTIC) is the most efficacious single chemotherapeutic agent for melanoma having an overall response rate of 24%. But the duration of response to DTIC is generally quite poor. Combination therapy with other synthetic and recombinant agents, including N,N'-bis(2-chloroethyl)-N-nitrosurea (carmustine, BCNU), cisplatin, tamoxifen, interferon-alpha (INF-α) and interleukin-2 (IL-2), has a higher response rate (e.g., 30-50%) in some trials, but a durable complete response rate is uncommon and toxicity is increased. Sequential chemotherapy has promise, but, clearly, current treatment options for individuals suffering from metastatic melanoma are unsatisfactory.

Various drugs derived from natural products, such as adriamycin (doxorubicin) derivatives, bleomycin, etoposide, and vincristine, and their derivatives, have been tested for efficacy against melanoma either as single agents or in combination therapy. However, similar to the synthetic and recombinant compounds, these compounds exhibit low response rates, transient complete responses, and high toxicities.

Nonetheless, as demonstrated by known and presently-used cancer chemotherapeutic agents, plant-derived natural products are a proven source of effective drugs. Two such useful natural product drugs are paclitaxel (taxol) and camptothecin. Paclitaxel originally derived from the bark of the Pacific yew tree *Taxus brevifolia* Nutt. (Taxaceae), currently is used for the treatment of refractory or residual ovarian cancer. More recently, clinical trials have been performed to investigate the possible role of paclitaxel in the treatment of metastatic melanoma. As a single agent, taxol displays activity comparable to cisplatin and IL-2. Taxol functions by a unique mode of action, and promotes the polymerization of tubulin. Thus, the antitumor response mediated by taxol is due to its antimitotic activity. The second drug of prominence, camptothecin, was isolated from the stem bark of a Chinese tree, *Camptotheca acuminata* Decaisne (Nyssaceae). Camptothecin also functions by a novel mechanism of action, i.e., the inhibition of topoisomerase I. Phase II trials of a water-soluble camptothecin pro-drug analog, Irinotican (CPT-11), have been completed in Japan against a variety of tumors with response rates ranging from 0% (lymphoma) to 50% (small cell lung). Topotecan, another water-soluble camptothecin analog, currently is undergoing Phase II clinical trials in the United States.

Previous antitumor data from various animal models utilizing betulinic acid have been extremely variable and apparently inconsistent. For example, betulinic acid was reported to demonstrate dose-dependent activity against the Walker 256 murine carcinosarcoma tumor system at dose levels of 300 and 500 mg/kg (milligrams per kilogram) body weight. In contrast, a subsequent report indicated the compound was inactive in the Walker 256 (400 mg/kg) and in the L1210 murine lymphocytic leukemia (200 mg/kg) models. Tests conducted at the National Cancer Institute confirmed these negative data.

Similarly, antitumor activity of betulinic acid in the P-388 murine lymphocyte test system has been suggested. However, activity was not supported by tests conducted by the National Cancer Institute. More recently, betulinic acid was shown to block phorbol ester-induced inflammation and epidermal ornithine decarboxylase accumulation in the mouse ear model. Consistent with these observations, the carcinogenic response in the two-stage mouse skin model was inhibited. Thus, some weak indications of antitumor activity by betulinic acid have been reported, but, until the present invention, no previous reports or data suggested that betulinic acid was useful for the selective control or treatment of human melanoma. Furthermore, to date, no information has been published with respect to the selective activity of derivatives of betulinic acid against melanoma cells.

SUMMARY OF THE INVENTION

The present invention is directed to a method and composition for preventing or inhibiting tumor growth. The active compound is betulinic acid or a derivative of betulinic acid. The betulinic acid is isolated by a method comprising the steps of preparing an extract from the stem bark of *Ziziphus mauritiana* and isolating the betulinic acid. Alternatively, betulin can be isolated from the extract and used as precursor for betulinic acid, which is prepared from betulin by a series of synthetic steps. The betulinic acid can be isolated from the extract by mediating a selective cytotoxic profile against human melanoma in a subject panel of human cancer cell lines, conducting a bioassay-directed fractionation based on the profile of biological activity using cultured human melanoma cells (MEL-2) as the monitor, and obtaining betulinic acid therefrom as the active compound. The resulting betulinic acid can be used to prevent or inhibit tumor growth, or can be converted to a derivative to prevent or inhibit tumor growth.

An important aspect of the present invention, therefore, is to provide a method and composition for preventing or inhibiting tumor growth and, particularly, for preventing or inhibiting the growth of melanoma using a natural product-derived compound, or a derivative thereof.

Another aspect of the present invention is to provide a treatment method using betulinic acid to prevent the growth or spread of cancerous cells, wherein the betulinic acid, or a derivative thereof, is applied in a topical preparation.

Another aspect of the present invention is to overcome the problem of high mammalian toxicity associated with synthetic anticancer agents by using a natural product-derived compound, e.g., betulinic acid or a derivative thereof.

Still another aspect of the present invention is to overcome the problem of insufficient availability associated with synthetic anticancer agents by utilizing readily available, and naturally occurring betulinic acid, or a derivative thereof.

Yet another aspect of the present invention is to prepare derivatives of betulinic acid that have a highly selective activity against melanoma cells, and that have physical properties that make the derivatives easier to incorporate into topical preparations useful for the prevention or inhibition of melanoma cell growth.

These and other aspects of the present invention will become apparent from the following description of the invention, which are intended to limit neither the spirit or scope of the invention but are only offered as illustrations of the preferred embodiments of the invention.

DETAILED DESCRIPTION OF THE PREFERRED EMBODIMENTS

Figure 1:
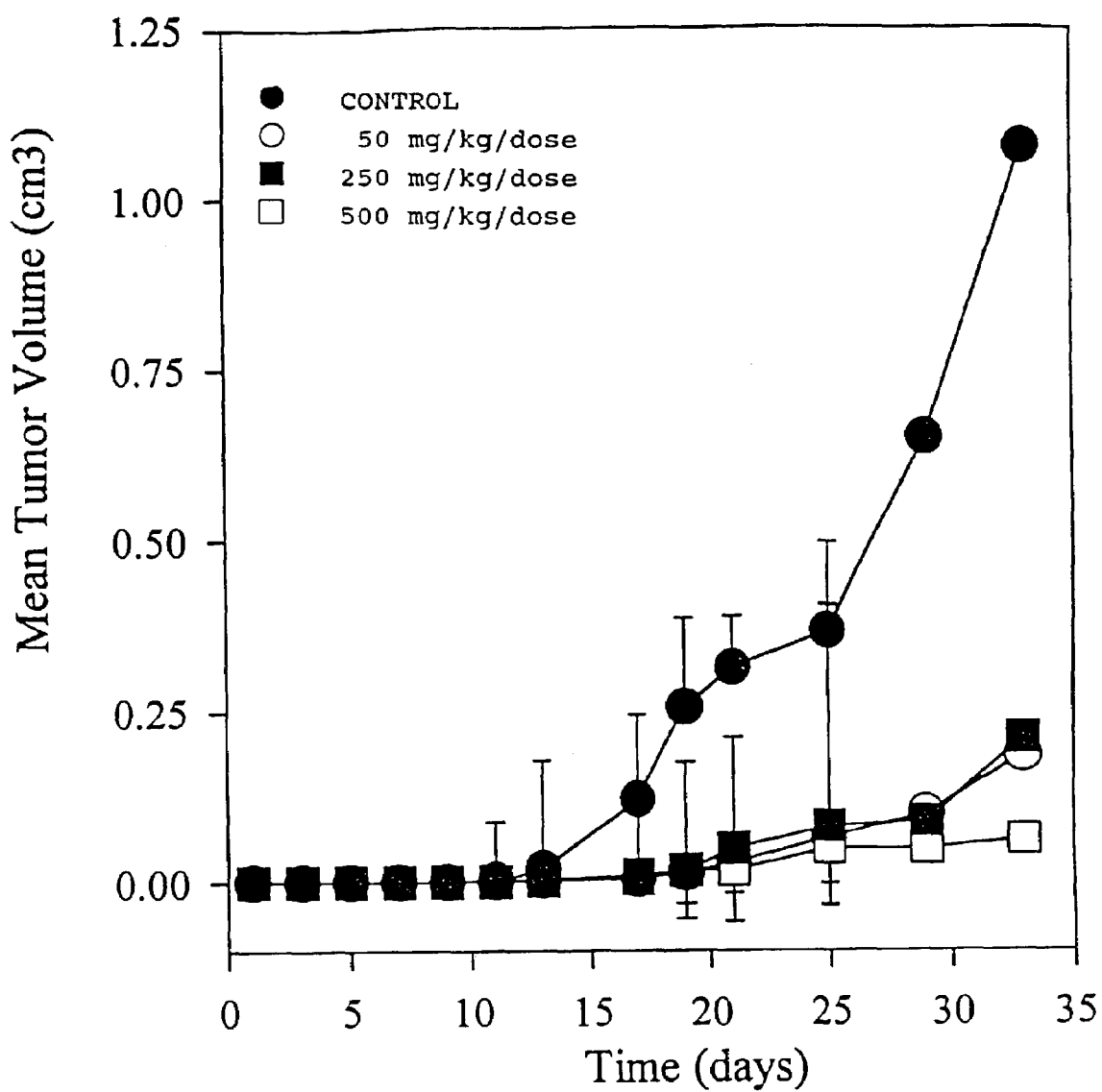
FIG. 1 is a plot of mean tumor volume (in cubic centimeters ($cm^3$)) vs. time for nonestablished MEL-2 tumors in control mice and mice treated with increasing dosages of betulinic acid.

Betulinic acid, 3β-hydroxy-lup-20(29)-ene-28-oic acid, is a natural product isolated from several genus of higher plants. Through a bioassay-directed fractionation of the stem bark of *Ziziphus mauritiana* Lam. (Rhamnaceae), betulinic acid, a pentacyclic triterpene, was isolated as an active compound that showed a selective cytotoxicity against cultured human melanoma cells. The cell lines evaluated for cytotoxicity were A431 (squamous), BC-1 (breast), COL-2 (colon), HT-1080 (sarcoma), KB (human oral epidermoid carcinoma), LNCaP (prostate), LU-1 (lung), U373 (glioma), and MEL-1, -2, -3, and -4 (melanoma). Betulinic acid was found to be an excellent antitumor compound against human melanoma due to its unique in vitro and in vivo cytotoxicity profile. Betulinic acid has shown a strong selective antitumor activity against melanoma by induction of apoptosis. The selective cytotoxicity of betulinic acid, and its lack of toxicity toward normal cells, afford a favorable therapeutic index. In addition, betulinic acid has been reported to have an anti-HIV activity.

The bark of white birch, *Betula alba*, contains betulin (up to about 25%), lup-20(29)-ene-3β,28-diol, and betulinic acid (0.025%), but it is difficult to isolate a sufficient quantity of betulinic acid to perform an extensive bioassay. It has been found that a quantity of betulinic acid could be provided from betulin through a simple synthetic approach. A number of multi-step synthetic conversions of betulin to betulinic acid have been reported, but these synthetic sequences suffer from a low overall yield. A concise two-step conversion of betulin to betulinic acid, in good yield, has been reported in *Synthetic Communications*, 27(9), pp. 1607-1612 (1997).

As shown in Table 1, in vitro growth of MEL-2 cells was inhibited by betulinic acid, i.e., an $ED_{50}$ value of about 2 µg/ml. However, none of the other cancer cell lines tested was affected by betulinic acid (i.e., $ED_{50}$ values of greater than 20 µg/ml). Such clearly defined cell-type specificity demonstrated by betulinic acid is both new and unexpected.

For example, as illustrated in Table 1, other known antitumor agents, such as paclitaxel, camptothecin, ellipticine, homoharringtonine, mithramycin A, podopyllotoxin, vinblastine and vincristine, demonstrated relatively intense, nonselective cytotoxic activity with no discernible cell-type selectivity. Moreover, the cytotoxic response mediated by betulinic acid is not exclusively limited to the MEL-2 melanoma cell line. Dose-response studies performed with additional human melanoma cell lines, designated MEL-1, MEL-3 and MEL-4, demonstrated $ED_{50}$ values of 1.1, 3.3 and 4.8 µg/ml, respectively.

In the following Table 1, the extracted betulinic acid and the other pure compounds were tested for cycotoxity against the following cultured human cell lines: A431 (squamous cells), BC-1 (breast), COL-2 (colon), HT-1080 (sarcoma), KB (human oral epidermoid carcinoma), LNCaP (prostate), LU-1 (lung), MEL-2 (melanoma), U373 (glioma) and ZR-75-1 (breast).

TABLE 1

Cytotoxic Activity Profile of the Crude Ethyl Acetate Extract Obtained from *Ziziphus mauritiana*, Betulinic acid, Other Antineoplastic Agents $ED_{50}$ (µg/ml)

| Compound | A431 | BC-1 | COL-2 | HT-1080 | KB | LNCaP | LU-1 | MEL-2 | U373 | ZR 75-1 |
|---|---|---|---|---|---|---|---|---|---|---|
| *Ziziphus mauritiana* crude extract | >20 | >20 | >20 | 9.5 | >20 | >20 | 5.2 | 3.7 | >20 | 15.8 |
| Betulinic acid | >20 | >20 | >20 | >20 | >20 | >20 | >20 | 2.0 | >20 | >20 |
| Taxol | 0.00 | 0.02 | 0.02 | 0.00 | 0.02 | 0.02 | 0.00 | 0.06 | 0.008 | 0.02 |
| Camptothecin | 0.00 | 0.07 | 0.005 | 0.01 | 0.00 | 0.006 | 0.00 | 0.02 | 0.000 | 0.001 |
| Ellipticine | 0.5 | 0.2 | 0.3 | 1.8 | 0.04 | 0.8 | 0.02 | 0.9 | 1.6 | 0.9 |
| Homoharringtonine | 0.02 | 0.03 | 0.1 | 0.01 | 0.00 | 0.03 | 0.03 | 0.04 | 0.2 | 0.06 |

TABLE 1-continued

Cytotoxic Activity Profile of the Crude Ethyl Acetate
Extract Obtained from Ziziphus mauritiana, Betulinic acid,
Other Antineoplastic Agents
$ED_{50}$ (µg/ml)

| Compound | A431 | BC-1 | COL-2 | HT-1080 | KB | LNCaP | LU-1 | MEL-2 | U373 | ZR 75-1 |
|---|---|---|---|---|---|---|---|---|---|---|
| Mithramycin A | 0.09 | 0.3 | 0.06 | 1.5 | 0.09 | 0.05 | 0.2 | 1.2 | 0.04 | 0.2 |
| Podophyllotoxin | 0.03 | 0.03 | 0.005 | 0.00 | 0.08 | 0.04 | 0.00 | 0.003 | 0.004 | 0.4 |
| Vinbiastine | 0.05 | 0.06 | 0.01 | 0.02 | 0.04 | 0.1 | 0.02 | 0.01 | 1.1 | 0.3 |
| Vincristine | 0.01 | 0.01 | 0.02 | 0.02 | 0.00 | 0.1 | 0.05 | 0.02 | 0.06 | 0.4 |

Betulinic acid (1) has the structural formula:

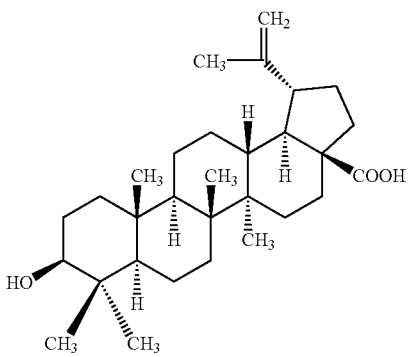

Betulinic acid is fairly widespread in the plant kingdom, and, as a compound frequently encountered, some previous biological activities have been reported.

Betulinic acid was obtained by extracting a sample of air-dried, milled stem bark (450 g) of Z. mauritiana with 80% aqueous methanol. The aqueous methanol extract then was partitioned successively with hexane and ethyl acetate to provide hexane, ethyl acetate and aqueous extracts. Among these extracts, the ethyl acetate (13.5 g) extract showed cytotoxic activity against a cultured melanoma cell line (MEL-2) with an $ED_{50}$ of 3.7 µg/ml. The ethyl acetate extract was chromatographed on a silica gel column using hexane-ethyl acetate (4:1 to 1:4) as eluent to give 10 fractions. Fractions 3 and 4 were combined and subjected to further fractionation to afford an active fraction (fraction 16) showing a major single spot by thin-layer chromatography [$R_f$ 0.67: $CHCl_3$:MeOH (chloroform:methanol) (10:1)], which yielded 72 mg of colorless needles after repeated crystallization from methanol (overall yield from dried plant material: 0.016% w/w).

As confirmed by the data summarized in Table 1, betulinic acid has been reported as noncytotoxic with respect to cultured KB cells. Cytotoxicity of the crude extracts and purified compounds was determined in a number of cultured human cancer cell lines. Table 1 sets forth the various types of cancer cells evaluated. The cells were cultured in appropriate media and under standard conditions. To maintain logarithmic growth, the media were changed 24 hours prior to cytotoxic assays. On the day of the assay, the cells were harvested by trypsinization, counted, diluted in media, and added to 96-well plates containing test compounds dissolved in DMSO; the final DMSO concentration was 0.05%.

The plates were incubated for three days. Following the incubation period, the cells were fixed and stained with sulforhodamine B (SRB) dye. The bound dye was liberated with Tris base, and the $OD_{515}$ was measured on an ELISA reader. The growth of the betulinic acid-treated cells was determined by the $OD_{515}$ values, and the growth was compared to the $OD_{515}$ values of DMSO-treated control cells. Dose response studies were performed to generate $ED_{50}$ values.

The isolated active compound, betulinic acid ($ED_{50}$ of 2.0 µg/ml for MEL-2), has a molecular formula of $C_{30}H_{48}O_3$, as determined by high-resolution mass spectral analysis, a melting point range of 292-293° C. (decomposition). The literature melting point range for betulinic acid is 290-293° C. A mixed melting point range with a known sample of betulinic acid was not depressed. The optical rotation of the compound was measured as +7.3° (c=1.2; pyridine) (lit. +7.5°). The identity of the isolated compound as betulinic acid was confirmed by comparing the above physical properties, as well as $^1$H-nmr, $^{13}$C-nmr and mass spectral data of the isolated compound, with physical data and spectra of a known sample of betulinic acid as reported in the literature.

To test the in vivo ability of betulinic acid to serve as an antineoplastic agent against malignant melanoma, a series of studies was performed with athymic (nude) mice injected subcutaneously with human melanoma cells (MEL-2). The initial study investigated the activity of betulinic acid against unestablished tumors. Treatment with betulinic acid began on day 1, i.e., 24 hours, following tumor cell injection. At doses of 50, 250, and 500 mg/kg (milligram per kilogram) body weight, betulinic acid demonstrated effective inhibition of tumor growth with p values of 0.001 for each dose versus a control (FIG. 1). These results indicate that betulinic acid can be used to prevent melanoma by topical application of melanoma. Such a discovery is important for individuals who are predisposed to melanoma due to hereditary or environmental factors.

In particular, the data plotted in FIG. 1 was derived from experiments wherein four week old athymic mice were injected subcutaneously in the right flank with $3.0 \times 10^8$ UISO MEL-2 cells. UISO MEL-2 is a cell line derived from metastatic melanoma from human pleural fluid. Drug treatment was initiated on the day following tumor cell injection and continued every fourth day for a total of six doses. Four control animals received 0.5 ml intraperitoneal (IP) of PVP control solution, while treated animals (4 per group) received 50, 250 or 500 mg/kg/dose IP betulinic acid/PVP in deionized $H_2O$. Betulinic acid was coprecipitated with PVP to increase solubility and bioavailability. The mice were weighed, and the tumors measured with a micrometer every other day throughout the study. All animals were sacrificed and autopsied on day 33, when the mean tumor volume in the control animals was approximately one $cm^3$.

There was greater inhibition of tumor growth at the highest dose of betulinic acid versus the lowest dose (p=0.04). Toxicity was not associated with the betulinic acid treatment because toxicity is indicated by loss of body weight or other forms of acute toxicity. No weight loss was observed.

Figure 2:
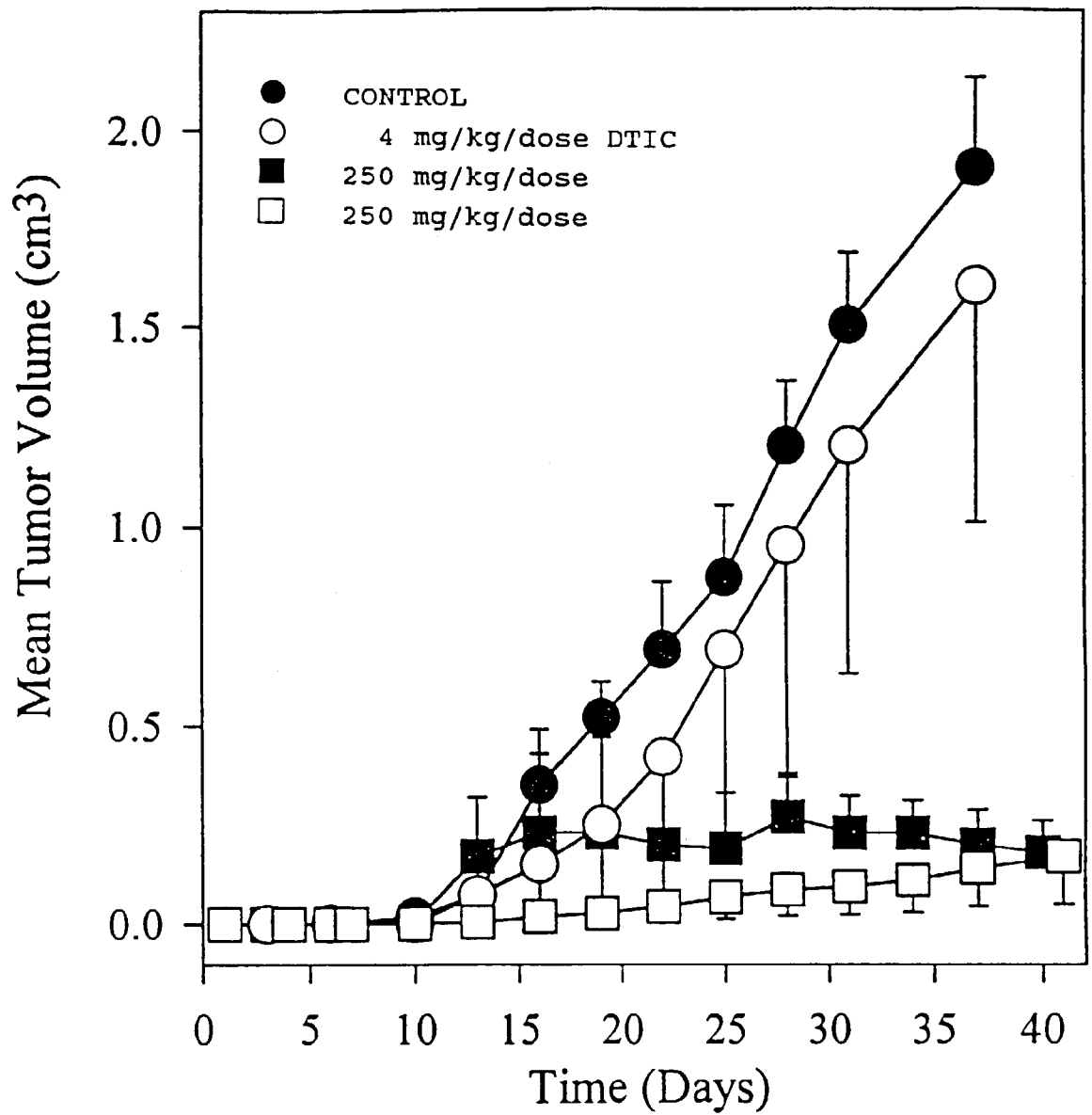
FIG. 2 is a plot of mean tumor volume (in $cm^3$) vs. time for established MEL-2 tumors in control mice and mice treated with DTIC or betulinic acid.

Next, in vivo testing of betulinic acid was performed on established melanomas. In this study, treatment was withheld until day 13, by which time a palpable tumor mass was present in all mice. As illustrated in FIG. 2, under these conditions betulinic acid successfully abrogated tumor growth (p=0.0001). Furthermore, tumor growth did not parallel that of the control (untreated) group even 14 days after the termination of treatment.

In particular, with respect to FIG. 2, four-week-old athymic mice were injected with $5 \times 10^8$ MEL-2 cells subcutaneously in the right flank. Four treatment groups of five mice each were studied. In one group, the mice received 250 mg/kg/dose of IP betulinic acid/PVP every third day for six total doses initiated the day following tumor cell injection. The control group received 0.5 ml IP saline. A DTIC treatment group received 4 mg/kg/dose IP DTIC every third day from day 13 to day 28 of the study. The betulinic acid treatment group received 250 mg/kg/dose IP betulinic acid/PVP every third day from day 13 to day 27. The control and DTIC-treated mice were sacrificed and autopsied on day 36 due to their large tumor burden. The remaining mice were sacrificed and autopsied on day 41.

As illustrated in FIG. 2, the efficacy of betulinic acid also was compared to DTIC, which is clinically available for the treatment of metastatic melanoma. The dose of DTIC, which is limited by toxicity, was selected to be equivalent to that administered to human patients. Tumor growth in the betulinic acid-treated group was significantly less than that observed in the DTIC-treated animals (p=0.0001). Compared to controls, DTIC produced a significant, but less pronounced, reduction in tumor growth, with a p value of 0.01. A fourth group in this study was treated with a schedule similar to that in the initial study. Under these conditions, betulinic acid, as demonstrated before, significantly inhibited tumor development (p=0.0001) and caused a prolonged reduction in tumor growth of up to three weeks following treatment termination.

Figure 4:
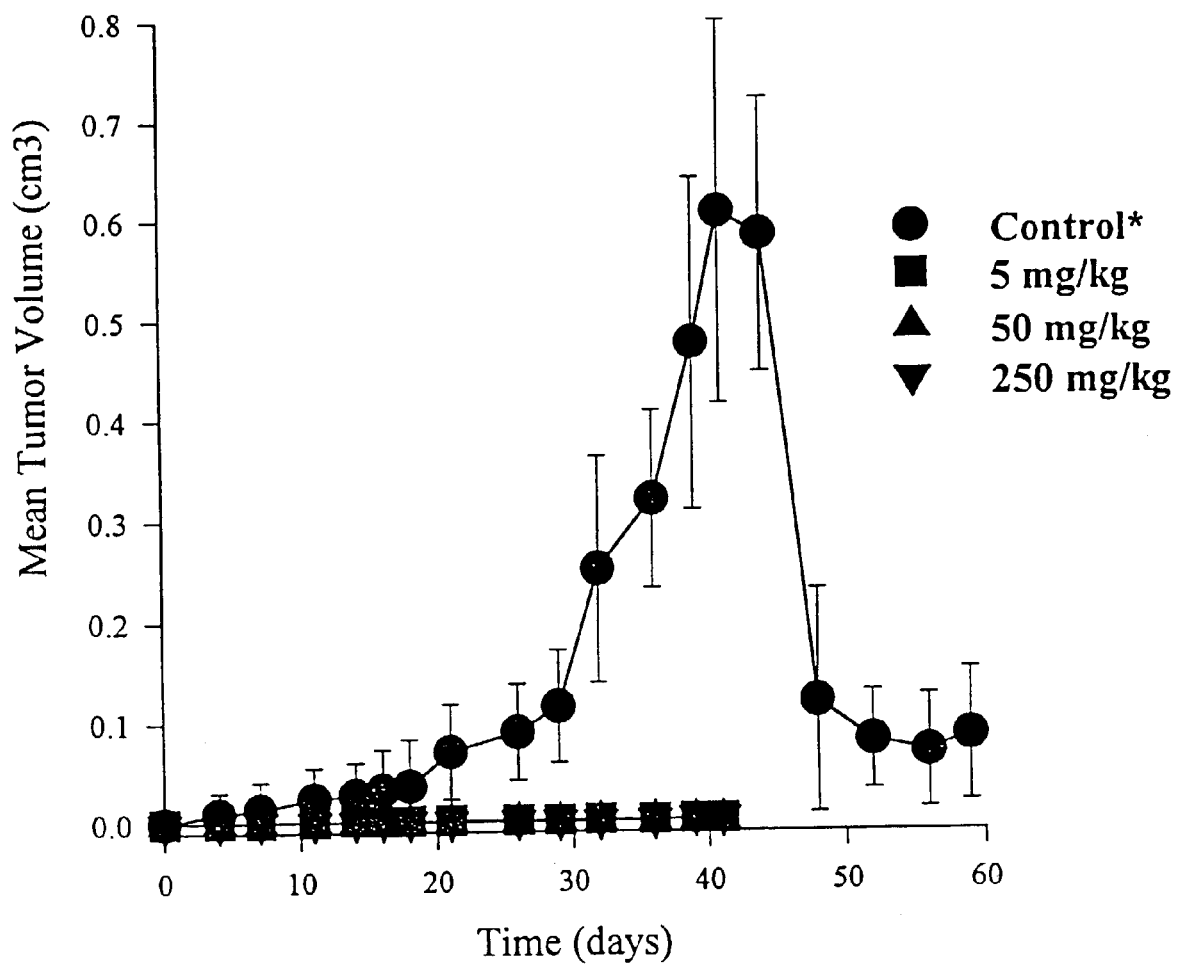
FIGS. 4 and 5 are plots of mean tumor volume ($cm^3$) vs. time for established and nonestablished MEL-1 tumors in control mice and mice treated with increasing doses of betulinic acid.
Figure 5:
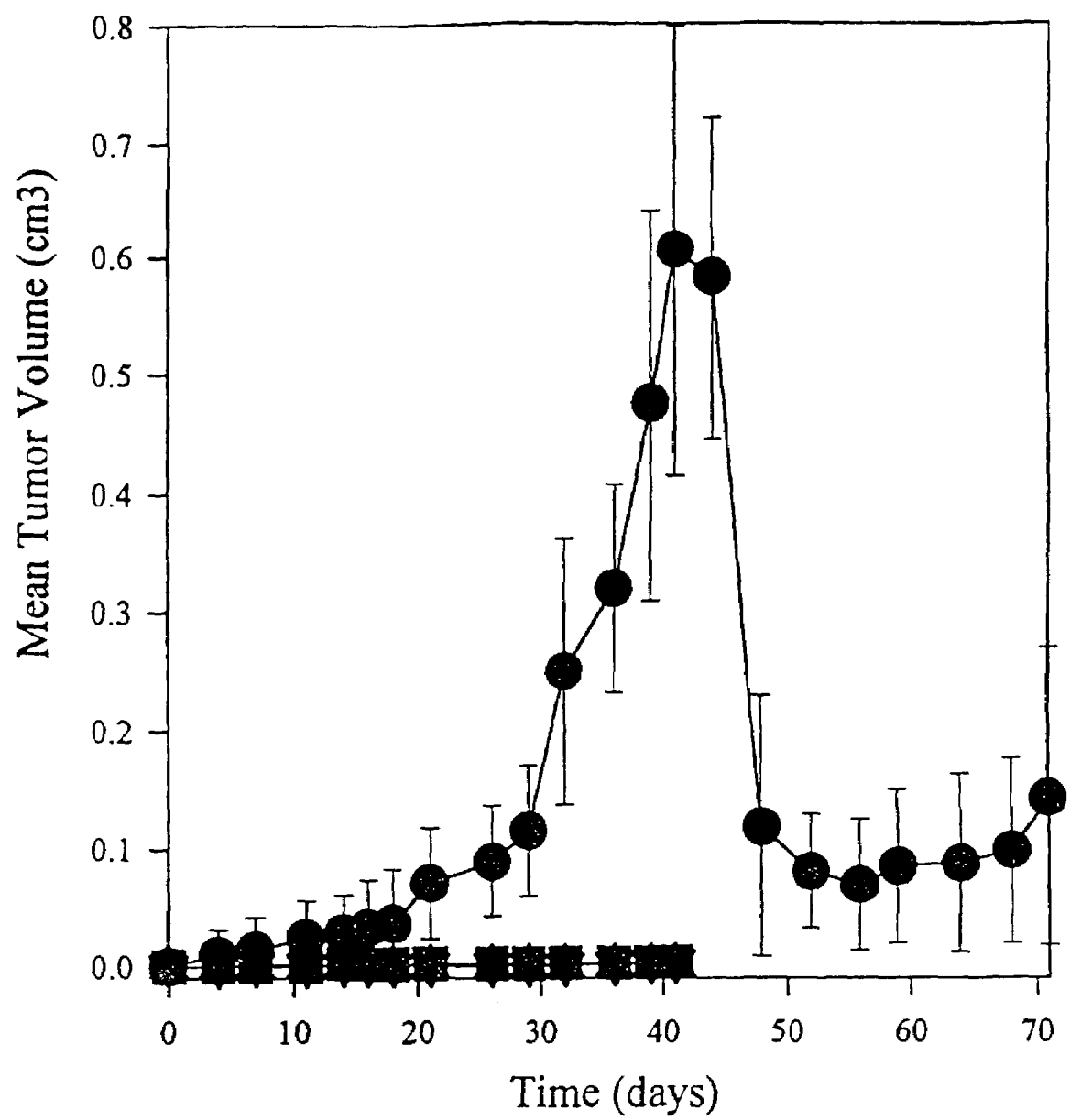

FIGS. 4 and 5 illustrate that betulinic acid also showed activity against MEL-1 cells. In particular, with respect to FIGS. 4 and 5, four week old athymic mice were injected subcutaneously in the right flank with $5.0 \times 10^8$ UISO MEL-1 cells. Drug treatment was initiated on the day following tumor cell injection and continued every fourth day for a total of six doses. Four control animals received 0.5 ml intraperitoneal (IP) saline, while treated animals (4 per group) received 5, 50 or 250 mg/kg/dose IP betulinic acid/PVP in dd $H_2O$. The mice were weighed, and tumors were measured with a micrometer every third day throughout the study. Treated animals were sacrificed and autopsied on day 41, when the mean tumor volume in the control mice was approximately 0.5 $cm^3$. The control mice then received six doses of 50 mg/kg every fourth day beginning day 41 and were sacrificed and autopsied on day 71.

The results illustrated in FIGS. 4 and 5 with respect to MEL-1 cells were similar to the results illustrated in FIGS. 1 and 2. Betulinic acid therefore is active both against MEL-1 and MEL-2 cells.

The mechanism by which antitumor agents mediated their activity is of great theoretical and clinical importance. Therefore, the mode of action by which betulinic acid mediates the melanoma-specific effect was investigated. Visual inspection of melanoma cells treated with betulinic acid revealed numerous surface blebs. This observation, as opposed to cellular membrane collapse, suggested the induction of apoptosis. One of the most common molecular and cellular anatomical markers of apoptosis is the formation of "DNA ladders," which correspond to the products of random endonucleolytic digestion of internucleosomal DNA. Although recent studies have shown that a lack of DNA laddering does not necessarily indicate a failure to undergo apoptosis, double-strand DNA scission that yields a fragment of about 50 kilobase pairs (Kbp) has been shown to consistently correlate with induction of apoptosis by various treatments in a variety of cell lines. Thus, generation of the 50 Kbp fragment is a reliable and general indicator of apoptosis. Generation of the fragment occurs upstream of the process leading to DNA ladders and represents a key early step in the commitment to apoptosis.

Therefore, an important feature of the present invention is a method of analyzing and quantifying the formation of the 50 Kbp fragment as a biomarker for induction of apoptosis in human cancer cell lines. This method comprises treatment of cells in culture, followed by analysis of the total cellular DNA content using agarose field-inversion gel electrophoresis. Under these conditions, the 50 Kbp fragment is resolved as a diffuse band. The fraction of the total cellular DNA represented by the 50 Kbp fragment is determined by densitometry on the contour of this band.

Figure 3:
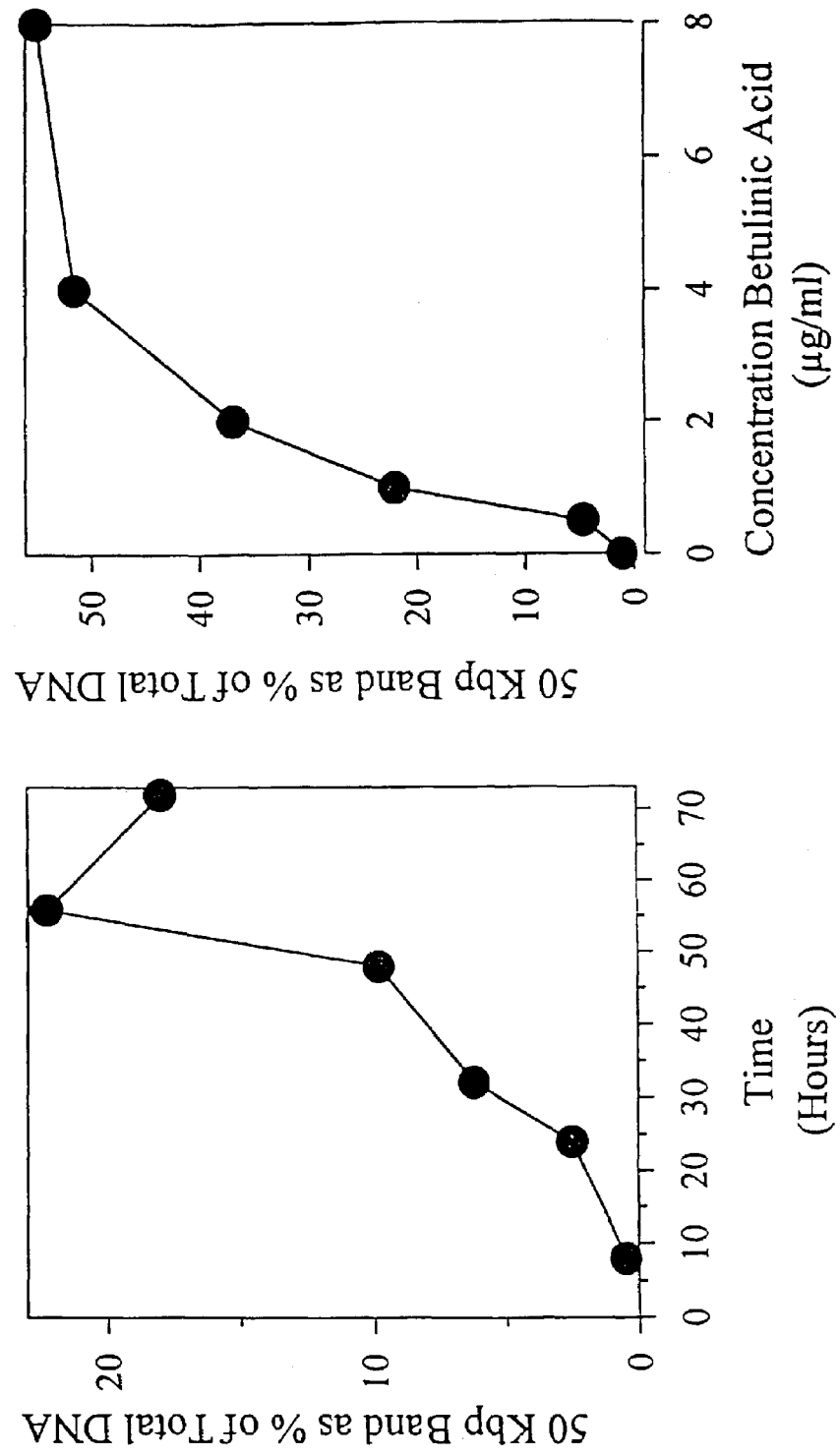
FIG. 3(A) is a plot of the 50 Kbp (kilobase pairs) band as % total DNA v. time for treatment of MEL-2 cells with 2 µg/ml (micrograms per milliliter) betulinic acid.
FIG. 3(B) is a plot of the 50 Kbp band as % total DNA versus concentration of betulinic acid (µg/ml)

To investigate the ability of betulinic acid to induce apoptosis, the above-described method was adapted for use with the MEL-2 cell line. As shown in FIG. 3A, time-dependent formation of a 50 Kbp DNA fragment was induced by betulinic acid with MEL-2 cells. Induction was at a maximum after a 56 hour treatment period. After this time period, a decline in the relative amount of the 50 Kbp fragment was observed, probably due to internal degradation. Also observed in the agarose gel were DNA fragments of about 146 and about 194 Kbp, which are theorized to be precursors in the process leading to the formation of the 50 Kbp fragment. Additionally, the induction of apoptosis (50 Kbp fragment) mediated by betulinic acid was dose-dependent (FIG. 3B), and the $ED_{50}$ value (about 1.5 μg/ml) observed in the apoptotic response closely approximated the $ED_{50}$ value previously determined for the cytotoxic response (Table 1).

With further respect to FIG. 3A, cultured MEL-2 cells ($10^6$ cells inoculated per 25 $cm^2$ flask) were treated with 2 g/ml betulinic acid (200 μg/ml DMSO, diluted 1:100 in media) for 24, 32, 48, 56 and 72 hours. After the treatment, the cells were harvested, collected by centrifugation, then snap frozen in liquid nitrogen for subsequent analysis. Samples were analyzed on a 1% agarose gel in a Hoefer HE100 SuperSub apparatus cooled to 10° C. by a circulating water bath. The electrode buffer was 0.5×TBE buffer containing 0.25 μg/ml ethidium bromide and was circulated during electrophoresis. Each gel included 20 μL Sigma Pulse Marker 0.1-200 Kbp DNA size markers. Prior to sample loading, 50 μL 2% SDS was added to each sample well. Each sample tube was rapidly thawed, then the pelleted cells were immediately transferred in a volume about 50 μL to the well containing SDS. Each well then was overlaid with molten LMP agarose, which was allowed to gel prior to placing the gel tray in the SuperSub apparatus.

Electrophoresis was performed at 172 volts for a total of 18 hours using two sequential field inversion programs with pulse ramping. The DNA/ethidium bromide fluorescence was excited on a UV transilluminator and photographed using Polaroid type 55 P/N film. The negative was analyzed using a PDI scanning densitometer and Quantity One software. The intensity of the 50 Kbp fragment was determined by measuring the contour optical density (OD×$mm^2$) as a percent of the total optical density in the sample lane, including the sample well. The decrease in the 50 Kbp band definition caused by internal degradation, and does not represent a reversal of the process.

With further respect to FIG. 3B, cultured MEL-2 cells were treated for 56 hours with the following concentrations of betulinic acid: 0, 0.1, 1.0, 2.0, 4.0 and 8.0 µg/ml. The cells were harvested and apoptosis measured as described for FIG. 3A. The experiment was repeated and a similar dose-response curve was observed (data not shown).

These data suggest a causal relationship, and it is theorized that betulinic acid-mediated apoptosis is responsible for the antitumor effect observed with athymic mice. Time-course experiments with human lymphocytes treated in the same manner with betulinic acid at concentrations of 2 and 20 µg/ml did not demonstrate formation of the 50 Kbp fragment (data not shown) indicating the specificity and possible safety of the test compound.

Taking into account a unique in vitro cytotoxicity profile, a significant in vivo activity, and mode of action, betulinic acid is an exceptionally attractive compound for treating human melanoma. Betulinic acid also is relatively innocuous toxicity-wise, as evidenced by repeatedly administering 500 mg/kg doses of betulinic acid without causing acute signs of toxicity or a decrease in body weight. Betulinic acid was previously found to be inactive in a Hippocratic screen at 200 and 400 mg/kg doses.

Betulinic acid also does not suffer from the drawback of scarcity. Betulinic acid is a common triterpene available from many species throughout the plant kingdom. More importantly, a betulinic acid analog, betulin, is the major constituent of white-barked birch species (up to 22% yield), and betulin can be converted to betulinic acid.

In addition to betulinic acid, betulinic acid derivatives can be used in a topically applied composition to selectively treat, or prevent or inhibit, a melanoma. Betulinic acid derivatives include, but are not limited to esters of betulinic acid, such as betulinic acid esterified with an alcohol having one to sixteen, and preferably one to six, carbon atoms, or amides of betulinic acid, such as betulinic acid reacted with ammonia or a primary or secondary amine having alkyl groups containing one to ten, and preferably one to six, carbon atoms.

Another betulinic acid derivative is a salt of betulinic acid. Exemplary, but nonlimiting, betulinic acid salts include an alkali metal salt, like a sodium or potassium salt; an alkaline earth metal salt, like a calcium or magnesium salt; an ammonium or alkylammonium salt, wherein the alkylammonium cation has one to three alkyl groups and each alkyl group independently has one to four carbon atoms; or transition metal salt.

Other betulinic acid derivatives also can be used in the composition and method of the present invention. One other derivative is the aldehyde corresponding to betulinic acid or betulin. Another derivative is acetylated betulinic acid, wherein an acetyl group is positioned at the hydroxyl group of betulinic acid.

In particular, betulinic acid derivatives have been synthesized and evaluated biologically to illustrate that betulinic acid derivatives possess selective antitumor activity against human melanoma cells lines in vitro. It has been demonstrated that modifying the parent structure of betulinic acid provides numerous betulinic acid derivatives that can be deused to prevent or inhibit malignant tumor growth, especially with respect to human melanoma. The antitumor activity of betulinic acid derivatives is important because betulinic acid, although exhibiting a highly selective activity against melanomas, also possesses a low water solubility. The low water solubility of betulinic acid, however, can be overcome by providing an appropriate derivative of betulinic acid. Modifying the parent structure betulinic acid structure also can further improve antitumor activity against human melanoma.

An examination of the structure of betulinic acid, i.e., compound (1), reveals that betulinic acid contains three positions, i.e., the C-3, C-20, and C-28 positions, where functional groups can be introduced. In addition, the introduced functional groups, if desired, then can be modified. Through a series of reactions at these three positions, a large number of betulinic acid derivatives were prepared and evaluated for bioefficacy against a series of human tumor cell lines, especially against human melanoma cell lines.

With respect to modifications at the C-3 position of betulinic acid, the hydroxyl group at the C-3 position can be converted to a carbonyl group by an oxidation reaction. The resulting compound is betulonic acid, i.e., compound (2). The ketone functionality of betulonic acid can be converted to oxime (3) by standard synthetic procedures. Furthermore, a large number of derivatives (4) can be prepared through substitution reactions performed on the hydroxyl group of oxime (3), with electrophiles, as set forth in equation (a):

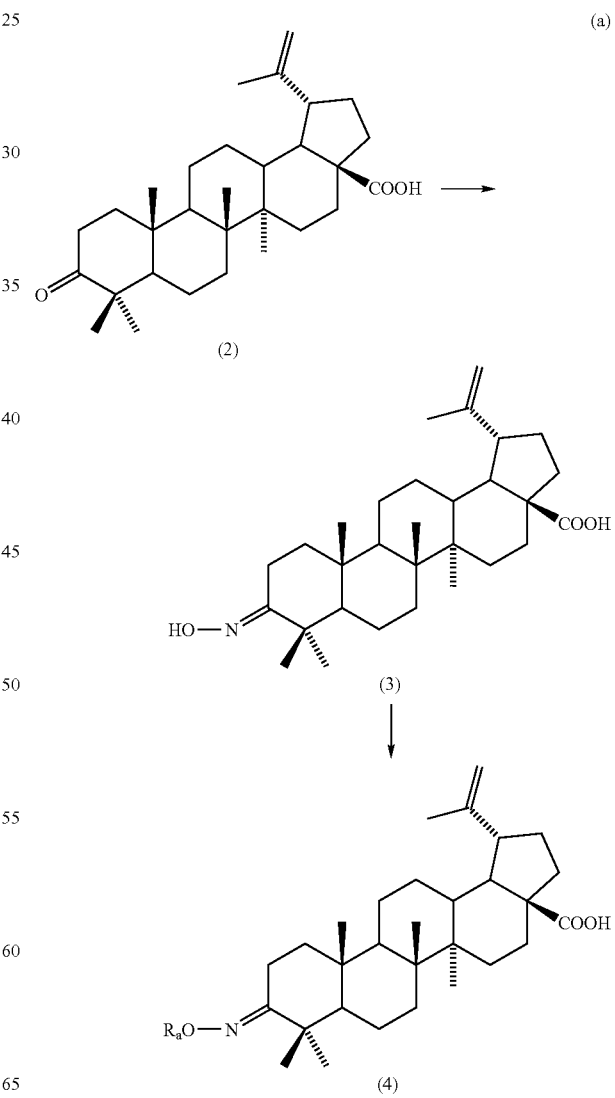

wherein $R_a$=H or $C_1$-$C_{16}$ alkyl, or $R_a$=$COC_6H_4X$, wherein X=H, F, Cl, Br, I, $NO_2$, $CH_3$, or $OCH_3$, or $R_a$=$COCH_2Y$, wherein Y=H, F, Cl, Br, or I, or $R_a$=$CH_2CHCH_2$ or $CH_2CCR_1$, wherein $R_1$ is H or $C_1$-$C_6$ alkyl. When $R_a$ is $C_1$-$C_{16}$ alkyl, preferred alkyl groups are $C_1$-$C_6$ alkyl groups.

The ketone functionality of betulonic acid can undergo a reductive amination reaction with various aliphatic and aromatic amines in the presence of sodium cyanoborohydride ($NaBH_3CN$) to provide the corresponding substituted amines (5) at the C-3 position, as set forth in equation (b).

(b)

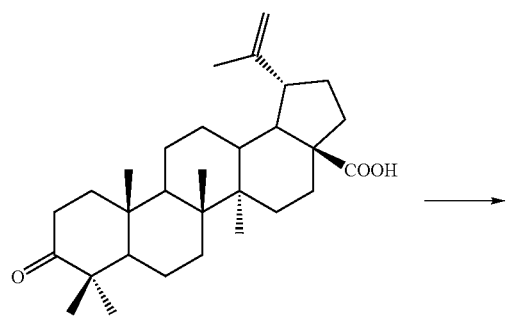

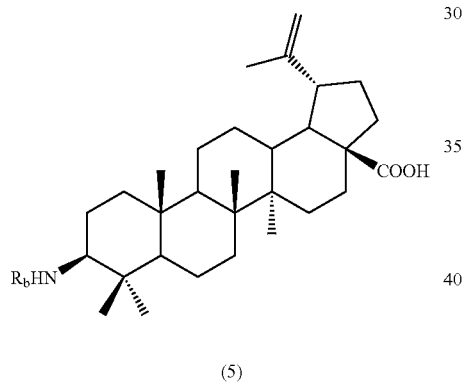

(5)

wherein $R_b$=H or $C_1$-$C_{10}$ alkyl, or $R_b$=$C_6H_4X$. A primary amine derivative, i.e., $R_b$=H, at the C-3 position can be reacted with a series of acyl chlorides or anhydrides, or alkyl halides, to provide amides and secondary amines (6), respectively, as set forth in equation (c).

(c)

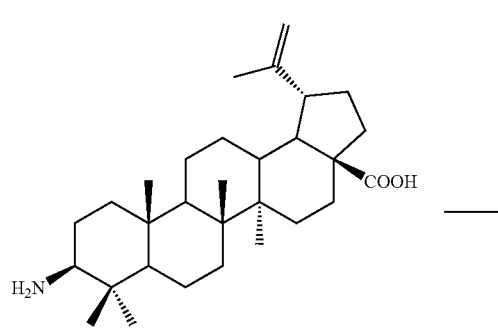

-continued

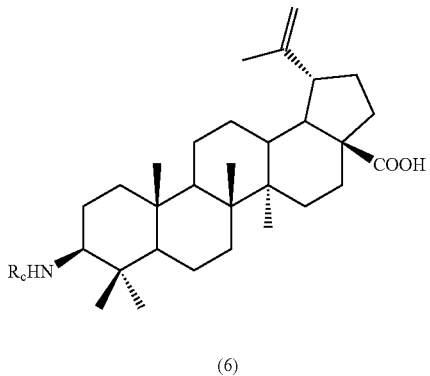

(6)

wherein $R_c$=$COC_6H_4X$, or $R_c$=$COCH_2Y$, or $R_c$=$CH_2CHCH_2$ or $CH_2CCR_1$.

The ketone functionality of betulonic acid can react with a series of lithium acetylides (i.e., LiC≡$CR_1$) to provide alkynyl alcohol derivatives (7) at the C-3 position. Based on the chemical reactivity and the stereoselectivity of the betulonic acid structure, α-alkynyl substituted β-hydroxyl alkynyl betulinic acid are the major products of the reaction, as set forth in equation (d).

(d)

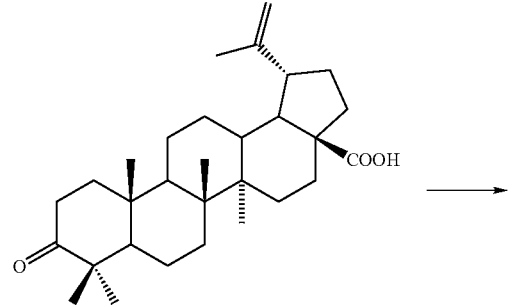

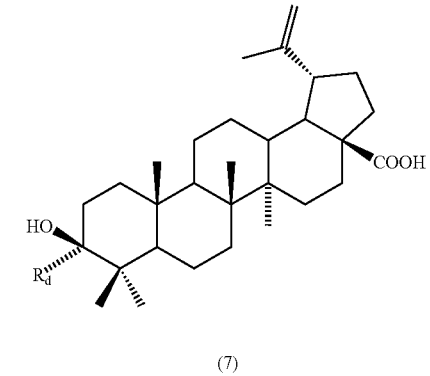

(7)

wherein $R_d$=$CCR_1$, wherein $R_1$ is H or $C_1$-$C_6$ alkyl.

A number of esters also can be prepared by reacting the hydroxyl group of betulinic acid with a variety of acyl chlorides or anhydrides (8), as set forth in equation (e).

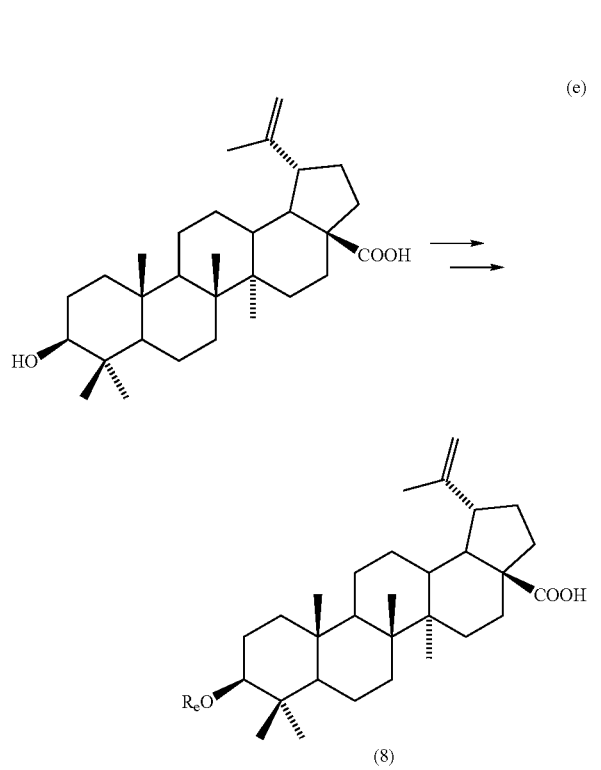

(e)

(8)

wherein $R_e = R_1CO$ or $XC_6H_4CO$.

With respect to modification at the C-28 position, the carboxyl group of betulinic acid can be converted to a number of esters (9) and amides (10) by reaction with an alcohol or an amine, respectively, as set forth in equations (f) and (g). Depending on the types of functional groups present on the alcohols or amines, additional structural modification are possible. The carboxyl group also can be converted to a salt, in particular an alkali metal salt, an alkaline earth salt, an ammonium salt, an alkylammonium salt, a hydroxyalkyl ammonium salt, or a transition metal salt.

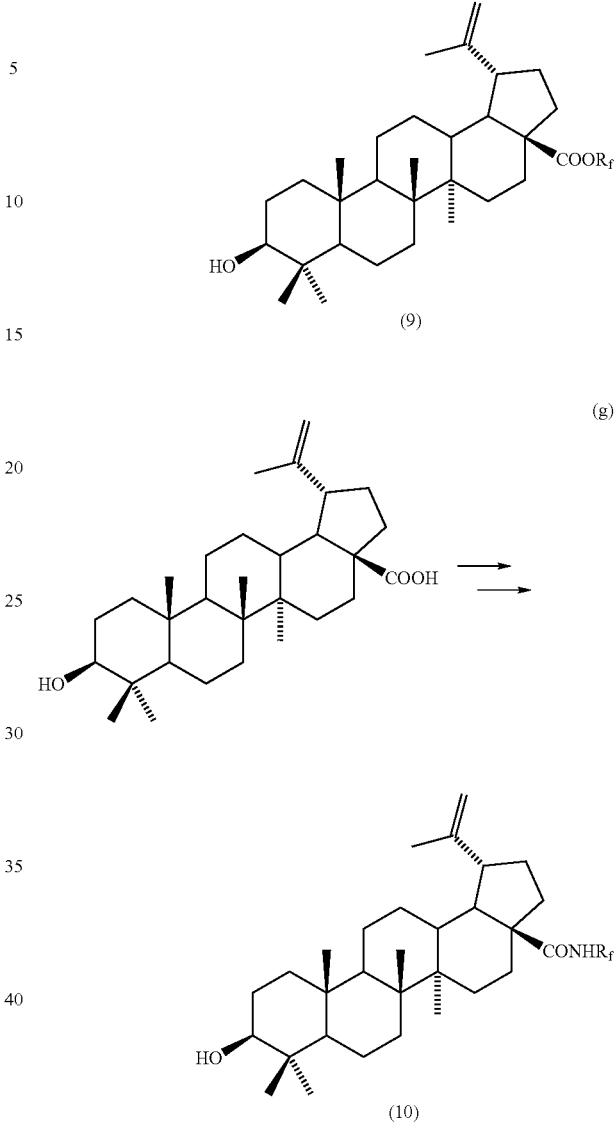

(f)

(9)

(g)

(10)

wherein $R_f = C_1$-$C_{10}$ alkyl, phenyl, substituted phenyl ($C_6H_4X$), or $CH_2CCR_1$.

The activated C-28 hydroxyl group of betulin can undergo substitution reactions, like SN-2 type reactions, with nucleophiles to provide an amino (11) or an ether derivative (12), as set forth in equations (h) and (i).

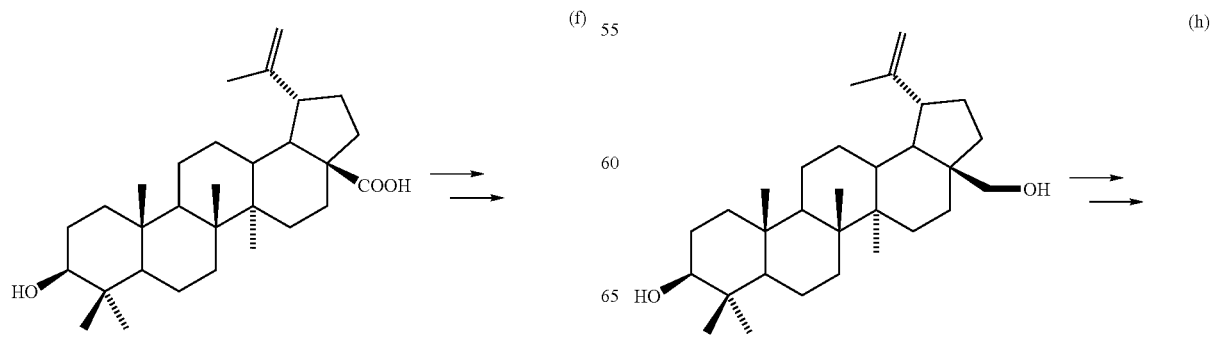

(h)

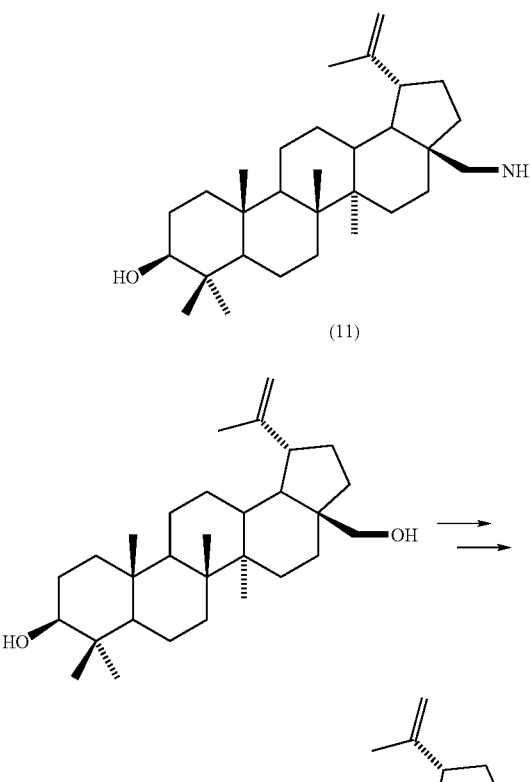

(11)

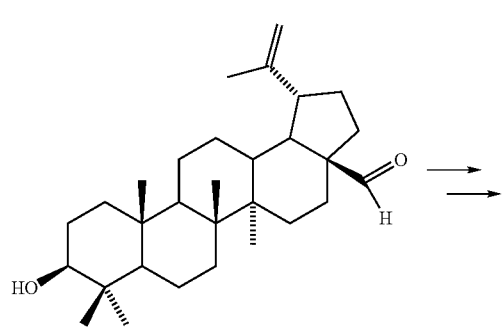

(12)

wherein $R_g$=H or $C_1$-$C_{16}$ alkyl, or $R_g$=$C_6H_4X$, and wherein $R_h$=$C_1$-$C_{16}$ alkyl or $C_6H_4X$.

The hydroxyl group at the C-28 position can be oxidized to yield an aldehyde, which in turn can react with hydroxylamine to provide a hydroxyloxime compound. The hydroxyloxime can react with a variety of electrophiles to provide the oxime derivatives (13), as set forth in equation (j).

(j)

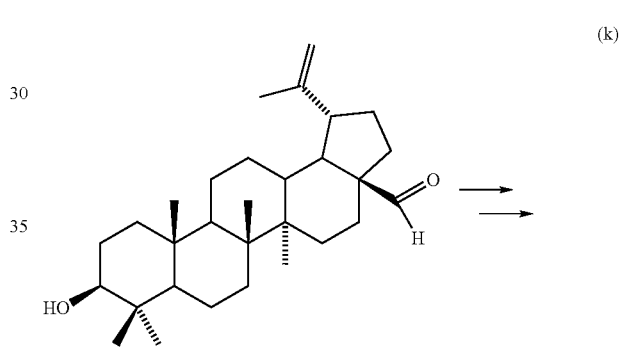

(13)

wherein $R_i$=H or $C_1$-$C_{16}$ alkyl, or $R_i$=$COC_6H_4X$, or $R_i$=$COCH_2Y$, or $R_i$=$CH_2CHCH_2$ or $CH_2CCR_1$.

The aldehyde at the C-28 position also can react with a series of lithium acetylide compounds to yield a variety of alkynyl betulin derivative (14), as set forth in equation (k).

(k)

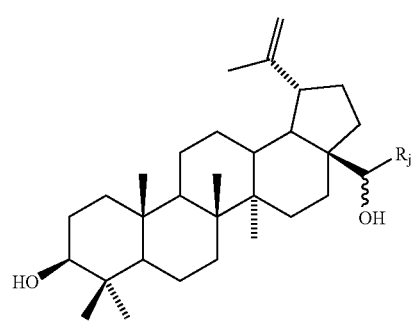

(14)

wherein $R_j$=$CCR_1$, wherein $R_1$=H or $C_1$-$C_6$ alkyl.

With respect to modifications at the C-20 position, the isoprenyl group at the C-20 position can be ozonized to yield a ketone (15) at C-20 position, as set forth in equation (1). A variety of reactions performed on the ketone functionality can provide a series of different derivatives. For example, the ketone functionality of compound (15) can be easily converted to a variety of oximes. Furthermore, a number of additional oxime derivatives (16) can be prepared through substitution reactions at the hydroxyl group of the hydroxyloxime with electrophiles, as set forth in equation (m).

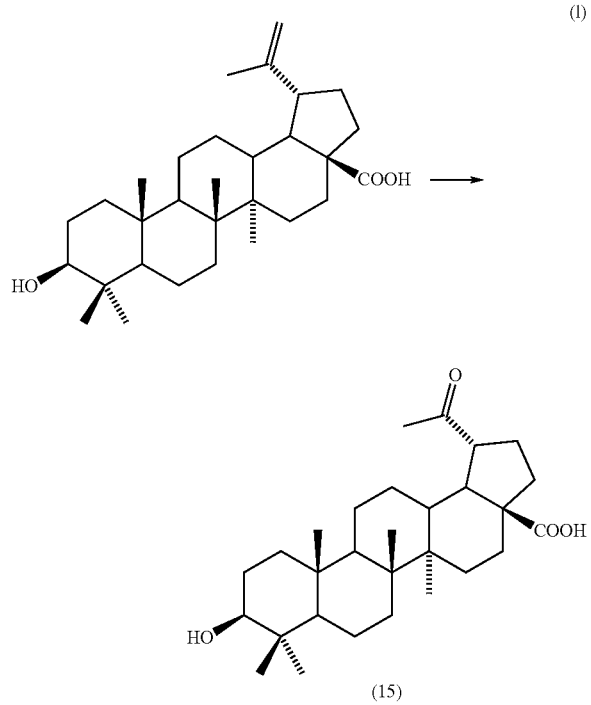

(l)

(m)

(15)

(16)

wherein $R_k$=H or $C_1$-$C_{16}$ alkyl, or $R_k$=$COC_6H_4X$ or $R_k$=$COCH_2Y$, or $R_k$=$CH_2CHCH_2$ or $CH_2CCR_1$.

The ketone functionality also can undergo a reductive amination reaction with a series of aliphatic and aromatic amines in the presence of $NaBH_3CN$ to provide a corresponding substituted amine (17) at the C-20 position, as set forth in equation (n).

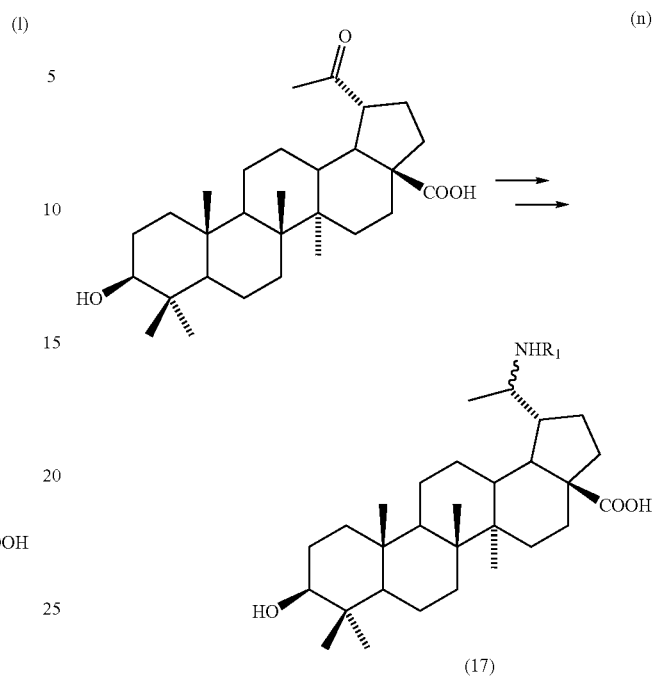

(n)

(17)

wherein $R_1$=$C_1$-$C_{16}$ alkyl, or $R_1$=$C_6H_4X$, or $R_1$=$COC_6H_4X$, or $R_1$=$COCH_2Y$, or $R_1$=$CH_2CHCH_2$ or $CH_2CCR_1$.

The ketone can be reacted with a series of lithium acetylides to provide alkynyl alcohol derivatives (18) at the C-20 position, as set forth in equation (o).

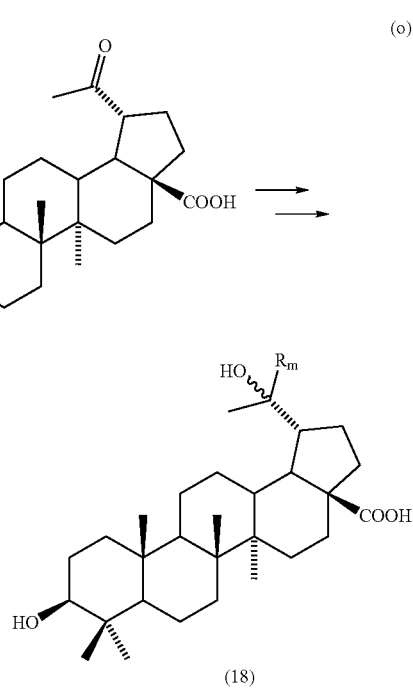

(o)

(18)

wherein, $R_m$=$CCR_1$.

The ketone further can be reduced to a secondary alcohol (19) to react with an acyl chloride to provide a series of esters (20) at the C-20 position, as set forth in equation (p).

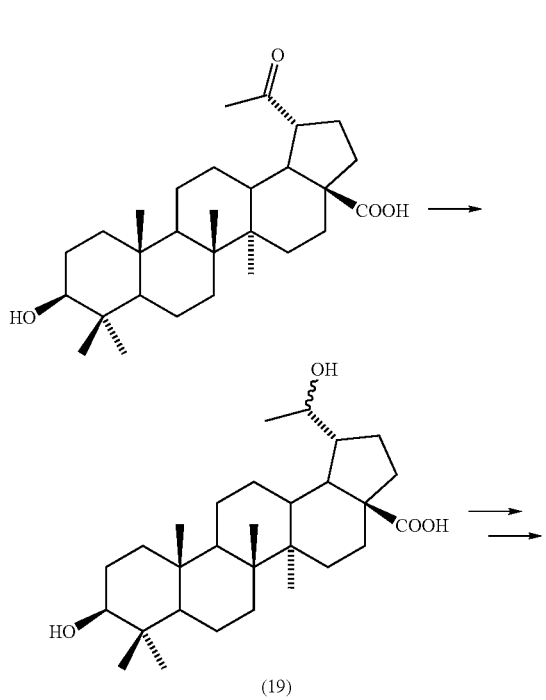

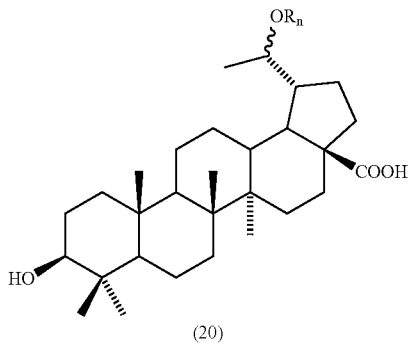

wherein $R_n$=H, $C_1$-$C_{16}$ alkyl, $CH_2CCR_1$, or $R_n$=$CH_3CO$ or $XC_6H_4CO$.

In addition, a number of different derivatives can be prepared through a combinatorial chemical approach. For example, as set forth below, in the preparation of oximes at the C-20 position, a number of electrophiles, e.g., a variety of alkyl halides, can be added together in one reaction vessel containing the hydroxyloxime to provide a mixture of betulinic acid derivatives. Each reaction product in the mixture can be isolated by using semi-preparative HPLC processes using appropriate separation conditions, then submitted for bioassay.

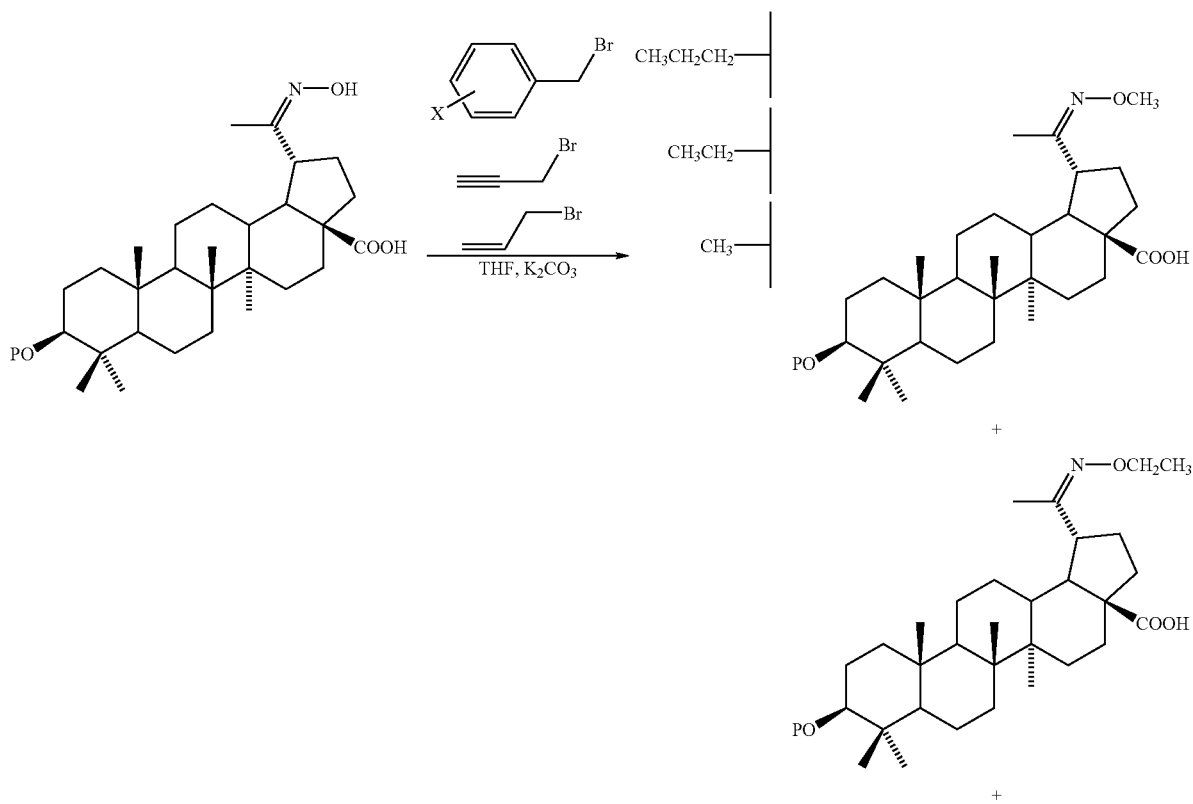

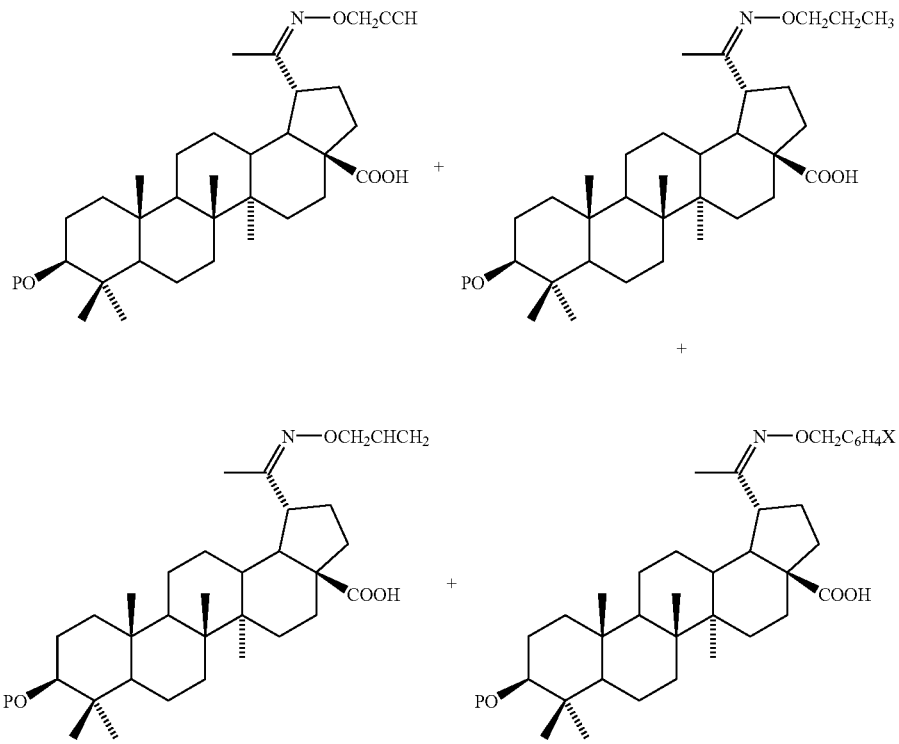

wherein P is a protecting group for the secondary alcohol functionality.

A low temperature reaction of betulonic acid with a mixture of lithium acetylides in a single reaction vessel, as set forth below, yielded a mixture of alkynyl alcohols at the C-3 position. Each component in the mixture can be isolated by using semi-preparative HPLC processes using appropriate separation conditions, then submitted for bioassay.

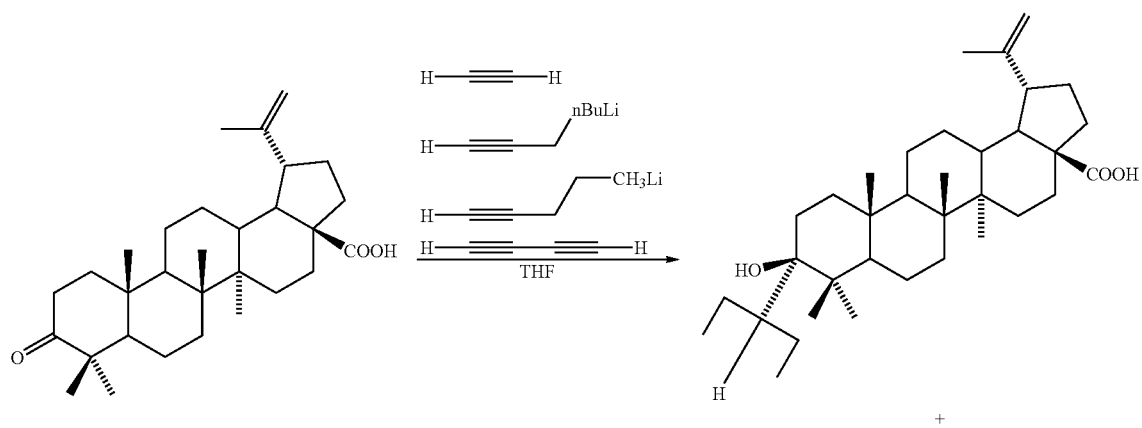

-continued

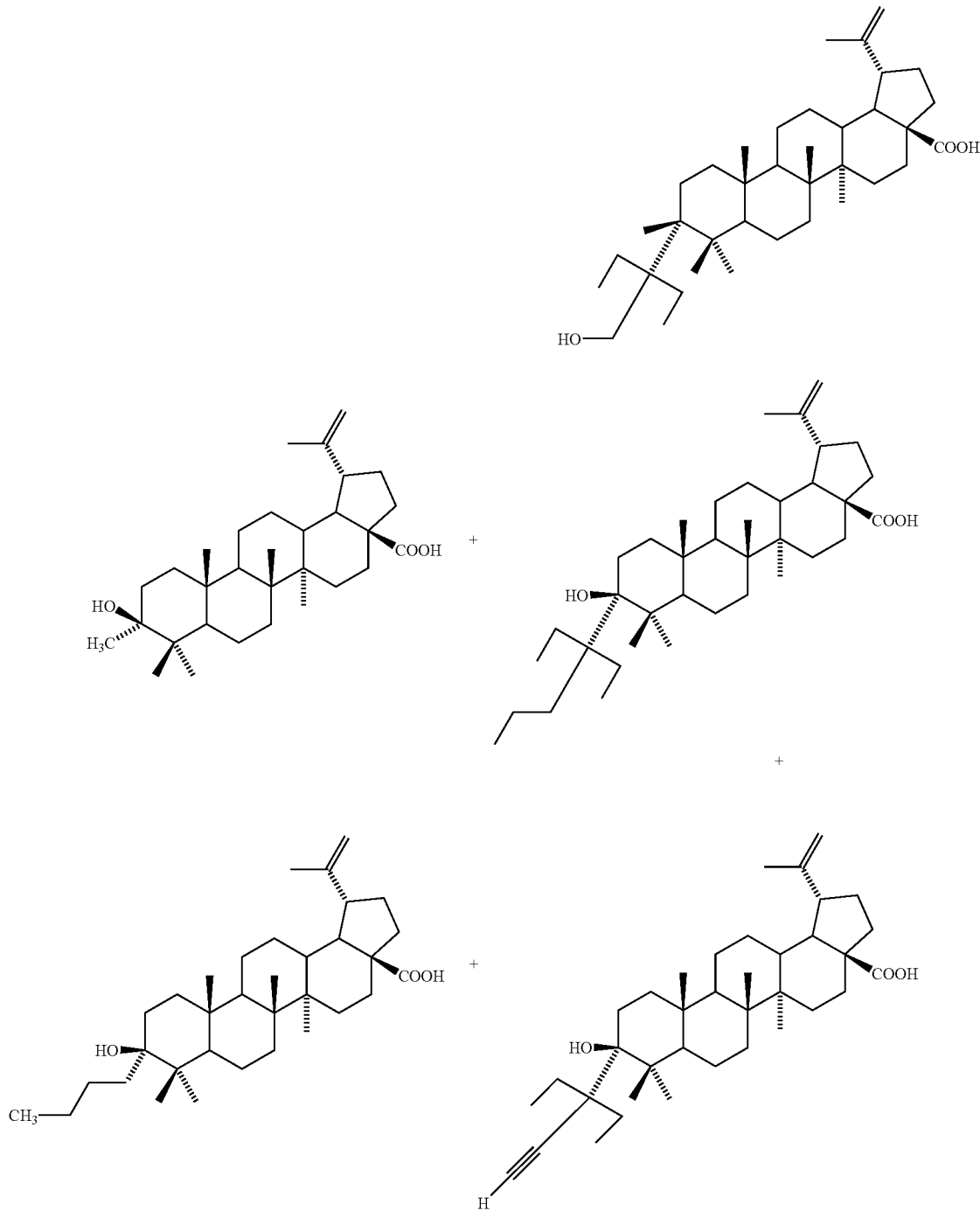

In order to demonstrate that betulinic acid derivatives have a potent bioefficacy, various derivatives were subjected to a series of biological evaluation tests. The biological evaluation of the derivatives focused on the activity against human melanoma cell lines. In particular, the following betulinic acid derivatives were prepared and tested for cytotoxicity profile against human melanoma cell lines and against a number of selected nonmelanoma cell lines. The results are summarized in Table 2. The data shows that some hydrogenated derivatives, i.e., compounds 5 and 11, are less active than nonhydrogenated derivatives 13 and 10, respectively. However, other hydrogenated derivatives, i.e., compounds 7 and 6, showed a comparable biological activity to nonhydrogenated derivatives 2 and 8, respectively. Therefore, it is possible to optimize the modification at the C-20 position to yield more potent betulinic acid derivatives. Table 3 contains a summary of data showing the effect of hydrogenation at the C-20 position.

TABLE 2

Cytotoxicity Data of Betulinic Acid Derivatives

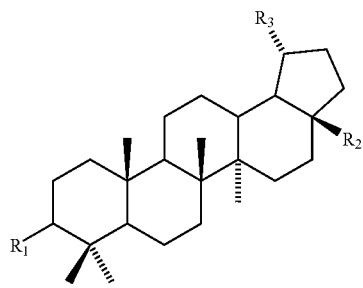

| | | | | ED$_{50}$ [μg/mL] (Std. Dev.) | | | | | |
|---|---|---|---|---|---|---|---|---|---|
| Compound | R$_1$ | R$_2$ | R$_3$ | MEL-2 | MEL-6 | MEL-8 | MALE-3M | LOX | KB |
| 1 | O= | CHO | CH$_2$=C(CH$_3$)$_2$ | 7.4 (2.4) | >20 | 3.2 (1.2) | >20 | 18.5 | 12.9 |
| 2 | HO—N= | COOH | CH$_2$=C(CH$_3$)$_2$ | 2.4 (0.3) | 14.8 (2.0) | 1.9 (1.0) | 15.8 | 9.1 | >20 |
| 3 | CH$_3$O—N= | CHNOCH$_3$ | CH$_2$=C(CH$_3$)$_2$ | >20 | >20 | >20 | >20 | >20 | 20 |
| 4 | HO—N= | CHNOH | CH$_2$=C(CH$_3$)$_2$ | 2.2 (0.7) | 11.9 (2.7) | 1.4 (0.6) | 17.5 | 4.1 | 3.3 |
| 5 | CH$_3$O—N= | COOH | C(CH$_3$)$_3$ | >20 | >20 | >20 | >20 | | |
| 6 (Dihydrobetulonic acid) | O= | COOH | C(CH$_3$)$_3$ | 0.7 (0.6) | 10.8 (2.6) | 0.9 (0.4) | 20 | | |
| 7 | HO—N= | COOH | C(CH$_3$)$_3$ | 2.2 (0.3) | 13.1 (1.1) | 1.6 (1.1) | 13.9 | | |
| 8 (Betulonic acid) | O= | COOH | CH$_2$=C(CH$_3$)$_2$ | 0.9 (0.8) | 15.3 (3.4) | 0.4 (0.1) | 20 | 6.9 | 2.5 |
| 9 | H$_2$N— | COOH | CH$_2$=C(CH$_3$)$_2$ | 1.3 (0.4) | 5.2 (2.6) | 1.3 (0.5) | 3.1 | | |
| 10 (Betulinic acid) | HO— | COOH | CH$_2$=C(CH$_3$)$_2$ | 1.2 (0.1) | 13.2 (1.5) | 1.0 (0.3) | 17.6 (0.5) | >20 | >20 |
| 11 (Dihydrobetulinic acid) | HO— | COOH | C(CH$_3$)$_3$ | 5.8 | | | | >20 | >20 |
| 12 (Betulin) | HO— | CH$_2$OH | CH$_2$=C(CH$_3$)$_2$ | >20 | | | | >20 | >20 |
| 13 | CH$_3$O—N= | COOH | CH$_2$=C(CH$_3$)$_2$ | 8.3 | | | | >20 | 4.3 |
| 14 (Methyl betulinate) | HO— | COOCH$_3$ | CH$_2$=C(CH$_3$)$_2$ | 8.3 | | | | 12.5 | 11.8 |
| 15 (Lupeol) | HO— | CH$_3$ | CH$_2$=C(CH$_3$)$_2$ | 17.6 | | | | 15.6 | >20 |
| 16 (Lupeol benzoate) | C$_6$H$_4$COO— | CH$_3$ | CH$_2$=C(CH$_3$)$_2$ | >20 | | | | >20 | >20 |

MEL-2, MEL-6, MEL-8, MALE-3M, and LOX are melanoma cell lines, and KB is human oral epidermoid carcinoma.

TABLE 3

Cytotoxicity Data of Betulinic Acid Derivatives (Effect of Hydrogenation at C-20)

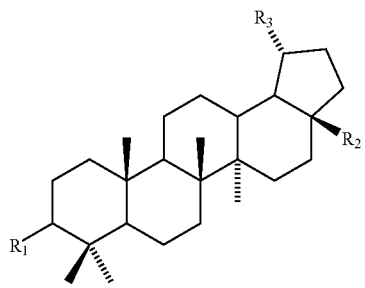

| | | | | ED$_{50}$ [μg/mL] (Std. Dev.) | | | | | |
|---|---|---|---|---|---|---|---|---|---|
| Compound | R$_1$ | R$_2$ | R$_3$ | MEL-2 | MEL-6 | MEL-8 | MALE-3M | LOX | KB |
| 13 | CH$_3$O—N= | COOH | CH$_2$=C(CH$_3$)$_2$ | 8.3 | | | | >20 | 4.3 |
| 5 | CH$_3$O—N= | COOH | C(CH$_3$)$_3$ | >20 | >20 | >20 | >20 | | |
| 10 (Betulinic acid) | HO— | COOH | CH$_2$=C(CH$_3$)$_2$ | 1.2 (0.1) | 13.2 (1.5) | 1.0 (0.3) | 17.6 (0.5) | >20 | >20 |

TABLE 3-continued

Cytotoxicity Data of Betulinic Acid Derivatives (Effect of Hydrogenation at C-20)

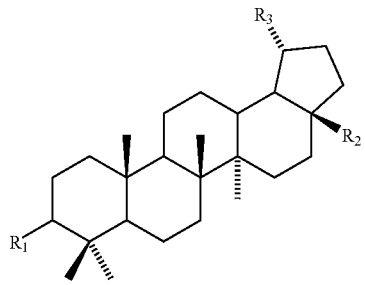

| Compound | $R_1$ | $R_2$ | $R_3$ | MEL-2 | MEL-6 | MEL-8 | MALE-3M | LOX | KB |
|---|---|---|---|---|---|---|---|---|---|
| 11 (Dihydrobetulinic acid) | HO— | COOH | $C(CH_3)_3$ | 5.8 | | | | >20 | >20 |
| 2 | HO—N= | COOH | $CH_2=C(CH_3)_2$ | 2.4 (0.3) | 14.8 (2.0) | 1.9 (1.0) | 15.8 | 9.1 | >20 |
| 7 | HO—N= | COOH | $C(CH_3)_3$ | 2.2 (0.3) | 13.1 (1.1) | 1.6 (1.1) | 13.9 | | |
| 8 (Betulonic acid) | O= | COOH | $CH_2=C(CH_3)_2$ | 0.9 (0.8) | 15.3 (3.4) | 0.4 (0.1) | 20 | 6.9 | 2.5 |
| 6 (Dihydrobetulonic acid) | O= | COOH | $C(CH_3)_3$ | 0.7 (0.6) | 10.8 (2.6) | 0.9 (0.4) | 20 | | |

The modification of betulinic acid at the C-3 position showed that all compounds, except methoxy oxime 13, expressed a comparable biological activity toward melanoma cell lines (Table 4). Amino compound 9 exhibited an improved cytotoxicity compared to betulinic acid 10. Compounds 2, 8, and 13 showed a decrease in selective cytotoxicity compared to betulinic acid.

With respect to modifications at the C-28 position, the free carboxylic acid group at C-28 position is important with respect to expression of biological activity (Table 5). However, it is unknown whether the size or the strength of hydrogen bonding or the nucleophilicity of the C-28 substituents is responsible for the biological effect.

TABLE 4

Cytotoxicity Data of Betulinic Acid Derivatives (Modification at C-3 Position)

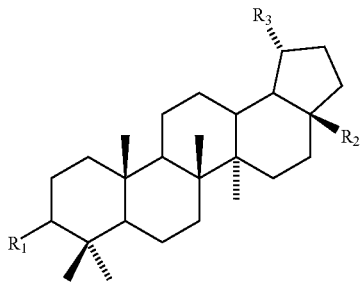

| Compound | $R_1$ | $R_2$ | $R_3$ | MEL-2 | MEL-6 | MEL-8 | MALE-3M | LOX | KB |
|---|---|---|---|---|---|---|---|---|---|
| 10 (Betulinic acid) | HO— | COOH | $CH_2=C(CH_3)_2$ | 1.2 (0.1) | 13.2 (1.5) | 1.0 (0.3) | 17.6 (0.5) | >20 | >20 |
| 8 (Betulonic acid) | O= | COOH | $CH_2=C(CH_3)_2$ | 0.9 (0.8) | 15.3 (3.4) | 0.4 (0.1) | 20 | 6.9 | 2.5 |
| 2 | HO—N= | COOH | $CH_2=C(CH_3)_2$ | 2.4 (0.3) | 14.8 (2.0) | 1.9 (1.0) | 15.8 | 9.1 | >20 |
| 13 | $CH_3O$—N= | COOH | $CH_2=C(CH_3)_2$ | 8.3 | | | | >20 | 4.3 |
| 9 | $H_2N$— | COOH | $CH_2=C(CH_3)_2$ | 1.3 (0.4) | 5.2 (2.6) | 1.3 (0.5) | 3.1 | | |

TABLE 5

Cytotoxicity Data of Betulinic Acid Derivatives (Modification at C-28 Position)

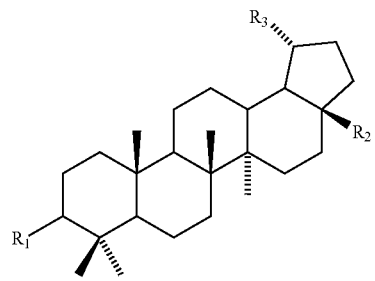

| Compound | $R_1$ | $R_2$ | $R_3$ | MEL-2 | MEL-6 | MEL-8 | MALE-3M | LOX | KB |
|---|---|---|---|---|---|---|---|---|---|
| | | | | \multicolumn{6}{c}{$ED_{50}$ [µg/mL] (Std. Dev.)} | | | | | |
| 12 (Betulin) | HO— | $CH_2OH$ | $CH_2=C(CH_3)_2$ | >20 | | | | >20 | >20 |
| 10 (Betulinic acid) | HO— | COOH | $CH_2=C(CH_3)_2$ | 1.2 (0.1) | 13.2 (1.5) | 1.0 (0.3) | 17.6 (0.5) | >20 | >20 |
| 14 (Methyl betulinate) | HO— | $COOCH_3$ | $CH_2=C(CH_3)_2$ | 8.3 | | | | 12.5 | 11.8 |
| 15 (Lupeol) | HO— | $CH_3$ | $CH_2=C(CH_3)_2$ | 17.6 | | | | 15.6 | >20 |

The biological activity changes attributed to oximes is illustrated in Table 6. The hydroxyloxime 4 improved the cytotoxicity profile, although selectivity was lost. It appears that the size of the substituent and its ability to hydrogen bond may influence the expression of the biological activity.

TABLE 6

Cytotoxicity Data of Betulinic Acid Derivatives (Effect by Oximes)

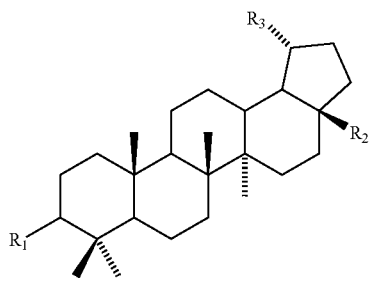

| Compound | $R_1$ | $R_2$ | $R_3$ | MEL-2 | MEL-6 | MEL-8 | MALE-3M | LOX | KB |
|---|---|---|---|---|---|---|---|---|---|
| | | | | \multicolumn{6}{c}{$ED_{50}$ [µg/mL] (Std. Dev.)} | | | | | |
| 12 (Betulin) | HO— | $CH_2OH$ | $CH_2=C(CH_3)_2$ | >20 | | | | >20 | >20 |
| 1 | O= | CHO | $CH_2=C(CH_3)_2$ | 7.4 (2.4) | >20 | 3.2 (1.2) | >20 | 18.5 | 12.9 |
| 4 | HO—N= | CHNOH | $CH_2=C(CH_3)_2$ | 2.2 (0.7) | 11.9 (2.7) | 1.4 (0.6) | 17.5 | 4.1 | 3.3 |
| 3 | $CH_3O$—N= | $CHNOCH_3$ | $CH_2=C(CH_3)_2$ | >20 | >20 | >20 | >20 | >20 | 20 |

The above tests show that modifying the parent structure of betulinic acid can provide derivatives which can be used as potent antitumor drugs against melanoma. Betulinic acid derivatives having a comparable or better antitumor activity than betulinic acid against human melanoma have been prepared. In addition, even though betulinic acid has a remarkably selective antitumor activity, betulinic acid also has a poor solubility in water. The low solubility of betulinic acid in water can be overcome by introducing an appropriate substituent on the parent structure, which in turn can further improve selective antitumor activity. In addition, because the parent compound, betulinic acid, has shown to possess anti-HIV activity, the derivatives also can be developed as potential anti-HIV drug candidates.

What is claimed is:

1. A composition for treating melanoma comprising betulinic acid modified at the C-3 position, said modified betulinic acid having a structure:

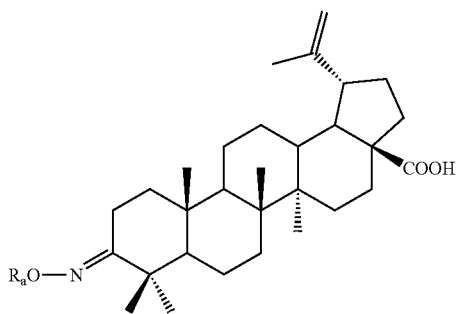

wherein $R_a$ is H, $C_1$-$C_{16}$ alkyl, $COC_6H_4X$, $COCH_2Y$, $CH_2CHCH_2$, or $CH_2C\equiv CR_1$, and wherein X is H, F, Cl, Br, I, $NO_2$, $CH_3$, or $OCH_3$, Y is H, F, Cl, Br, or I, and $R_1$ is H or $C_1$-$C_6$ alkyl.

2. A composition for treating melanoma comprising betulinic acid modified at the C-3 position, said modified betulinic acid having a structure:

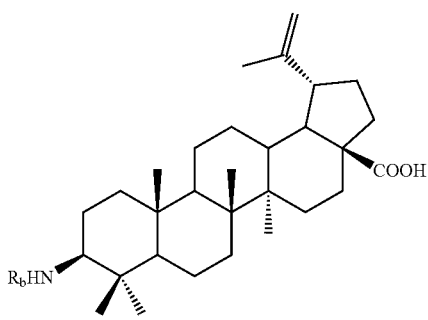

wherein $R_b$ is $COC_6H_4X$, $COCH_2Y$, $CH_2CH=CH_2$, or $CH_2C\equiv CR_1$, and wherein X is H, F, Cl, Br, I, $NO_2$, $CH_3$, or $OCH_3$, Y is H, F, Cl, Br, or I, and $R_1$ is H or $C_1$-$C_6$ alkyl.

3. A composition for treating melanoma comprising betulinic acid modified at the C-3 position, said modified betulinic acid having a structure:

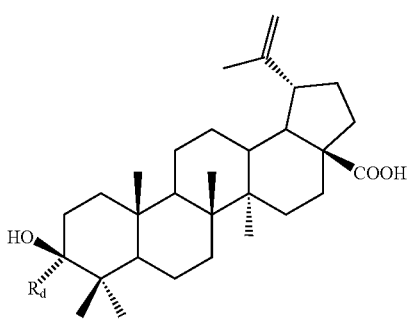

wherein $R_d$ is $C=CR_1$, and wherein $R_1$ is H or $C_1$-$C_6$ alkyl.

4. A composition for treating melanoma comprising betulinic acid modified at the C-3 position, said modified betulinic acid having a structure:

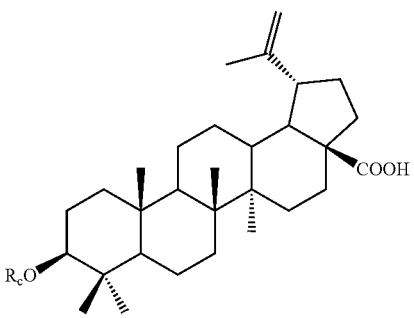

wherein $R_e$ is $R_1CO$ or $COC_6H_4X$, $R_1$ is H, and X is H, F, Cl, Br, I, $NO_2$, $CH_3$, or $OCH_3$.

5. A method of inhibiting growth of a melanoma comprising topically applying a therapeutically effective amount of the composition of claim 1, 2, or 3 to the melanoma.

6. A composition for treating melanoma comprising betulinic acid modified at the C-28 position, said modified betulinic acid having a structure:

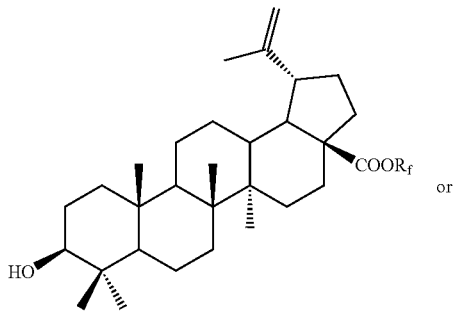

wherein $R_f$ is $CH_2C\equiv CR_1$ and $R_1$ is H or $C_1$-$C_6$ alkyl.

7. A composition for treating melanoma comprising betulinic acid modified at the C-28 position, said modified betulinic acid having a structure:

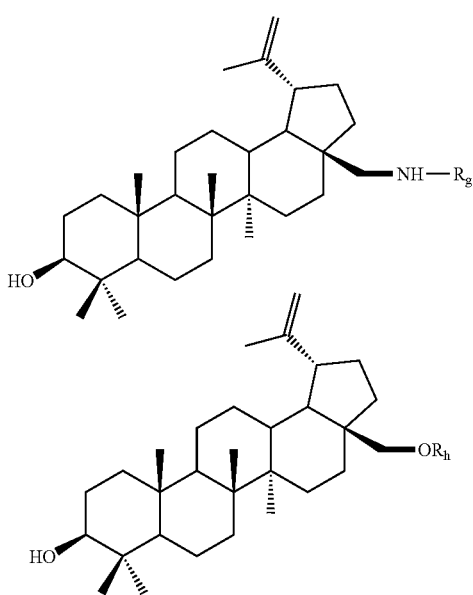

wherein $R_g$ is H, $C_1$-$C_6$ alkyl, or $C_6H_4X$, $R_h$ is $C_1$-$C_{16}$ alkyl or $C_6H_4X$, and wherein X is H, F, Cl, Br, I, $NO_2$, $CH_3$, or $OCH_3$.

8. A composition for treating melanoma comprising betulinic acid modified at the C-28 position, said modified betulinic acid having a structure:

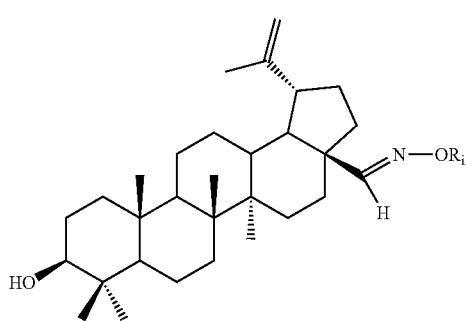

wherein $R_i$, is $COC_6H_4X$, $COCH_2Y$, $CH_2CH{=}CH_2$, or $CH_2C{\equiv}CR_1$, and wherein X is H, F, Cl, Br, I, $NO_2$, $CH_3$, or $OCH_3$, Y is H, F, Cl, Br, or I, and $R_1$ is H or $C_1$-$C_6$ alkyl.

9. A composition for treating melanoma comprising betulinic acid modified at the C-28 position, said modified betulinic acid having a structure:

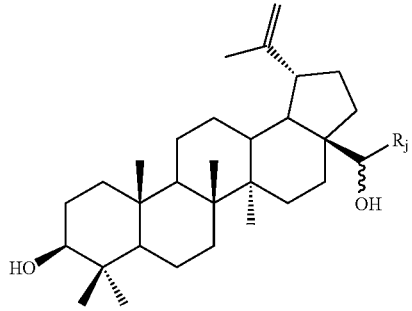

wherein $R_j$ is $C{\equiv}CR_1$ and wherein $R_1$ is H or $C_1$-$C_6$ alkyl.

10. A method of inhibiting growth of a melanoma comprising topically applying a therapeutically effective amount of the composition of claim 6, 7, 8, or 9 to the melanoma.

11. A method of inhibiting growth of a melanoma comprising topically applying a therapeutically effective amount of a composition comprising betulinic acid modified at the C-20 position, said modified betulinic acid having a structure:

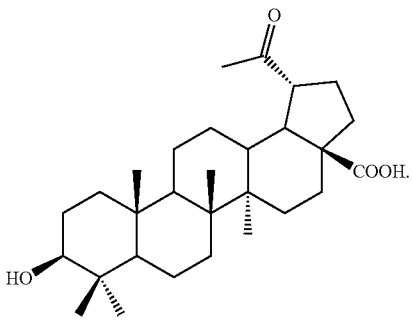

12. A composition for treating melanoma comprising betulinic acid modified at the C-20 position, said modified betulinic acid having a structure:

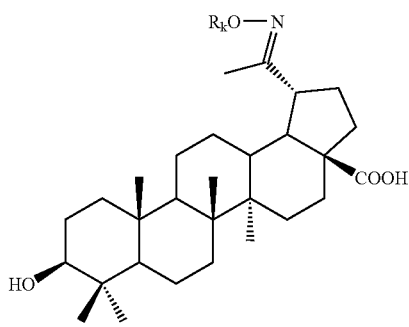

wherein $R_k$ is H, $C_1$-$C_{16}$ alkyl, $COC_6H_4X$, $COCH_2Y$, $CH_2CH{=}CH_2$, $CH_2C{\equiv}CH_1$, and wherein X is H, F, Cl, Br, I, $NO_2$, $CH_3$, or $OCH_3$, Y is H, F, Cl, Br, or I, and $R_1$ is H or $C_1$-$C_6$ alkyl.

13. A composition for treating melanoma comprising betulinic acid modified at the C-20 position, said modified betulinic acid having a structure:

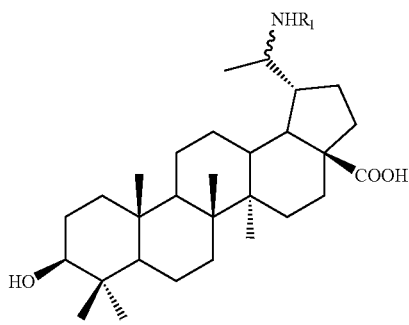

wherein $R_p$ is $C_1$-$C_{16}$ alkyl, $C_6H_4X$, $COC_6H_4X$, $COCH_2Y$, $CH_2CH{=}CH_2$, or $CH_2C{\equiv}CR_1$, and
wherein X is H, F, Cl, Br, I, $NO_2$, $CH_3$, or $OCH_3$, Y is H, F, Cl, Br, or I, and $R_1$ is H or $C_1$-$C_{16}$ alkyl.

14. A composition for treating melanoma comprising betulinic acid modified at the C-20 position, said modified betulinic acid having a structure:

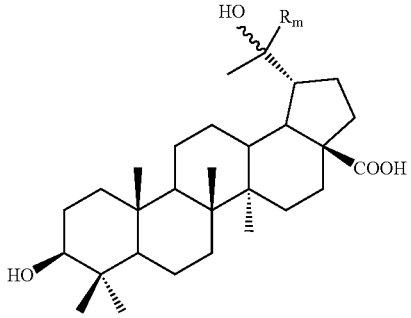

wherein $R_m$ is C≡$CR_1$ and $R_1$ is H or $C_1$-$C_6$ alkyl.

15. A composition for treating melanoma comprising betulinic acid modified at the C-20 position, said modified betulinic acid having a structure:

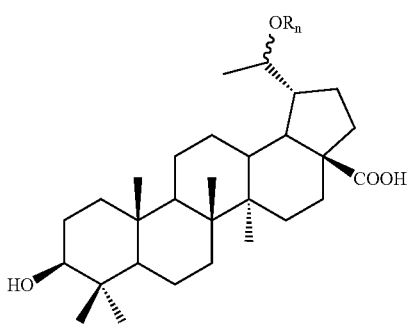

wherein $R_n$ is H, $C_1$-$C_{16}$ alkyl, $CH_2$C≡$CR_1$, $CH_3$CO, or $COC_6H_4X$, and wherein $R_1$ is H or $C_1$-$C_6$ alkyl, and X is H, F, Cl, Br, I, $NO_2$, $CH_3$, or $OCH_3$.

16. A method of inhibiting growth of a melanoma comprising topically applying a therapeutically effective amount of the composition of claim 12, 13, 14, or 15 to the melanoma.

17. A composition for treating melanoma comprising a compound having a structure:

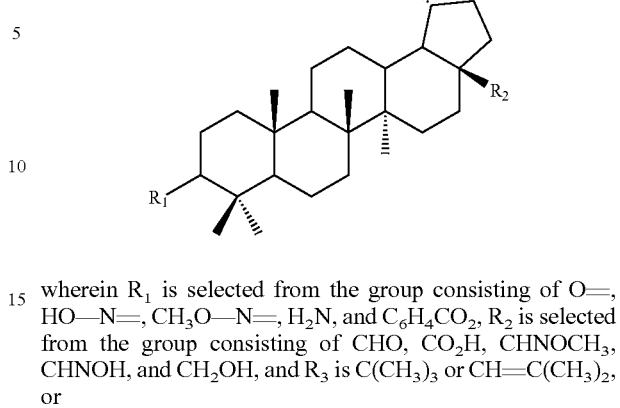

wherein $R_1$ is selected from the group consisting of O=, HO—N=, $CH_3$O—N=, $H_2$N, and $C_6H_4CO_2$, $R_2$ is selected from the group consisting of CHO, $CO_2$H, $CHNOCH_3$, CHNOH, and $CH_2$OH, and $R_3$ is $C(CH_3)_3$ or CH=$C(CH_3)_2$, or wherein $R_1$ is selected from the group consisting of O=, HO—N=, $CH_3$O—N=, $H_2$N, HO, and $C_6H_4CO_2$, $R_2$ is selected from the group consisting of CHO, $CHNOCH_3$, CHNOH, and $CH_2$OH, and $R_3$ is $C(CH_3)_3$ or CH=$C(CH_3)_2$.

18. A method of inhibiting growth of a melanoma comprising topically applying a therapeutically effective amount of the composition of claim 17 to the melanoma.

19. A method of inhibiting growth of a melanoma comprising topically applying a therapeutically effective amount of a composition comprising betulinic acid modified at the C-3 position, said modified betulinic acid having a structure:

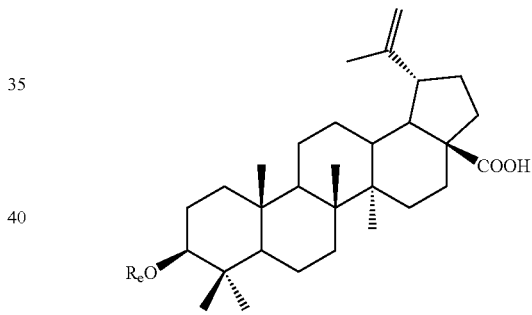

wherein $R_e$ is $R_1$CO or $COC_6H_4X$, $R_1$ is H, and X is H, F, Cl, Br, I, $NO_2$, $CH_3$, or $OCH_3$.

* * * * *

UNITED STATES PATENT AND TRADEMARK OFFICE
CERTIFICATE OF CORRECTION

PATENT NO. : 7,414,042 B2 Page 1 of 2
APPLICATION NO. : 10/317361
DATED : August 19, 2008
INVENTOR(S) : John M. Pezzuto et al.

It is certified that error appears in the above-identified patent and that said Letters Patent is hereby corrected as shown below:

On the Title Page:
Item (*), add -- This patent is subject to a terminal disclaimer. --.

Item (57), line 4, "topically is inserted therefore." should be -- topically. --.

In the Claims:
At Column 32, line 16, " 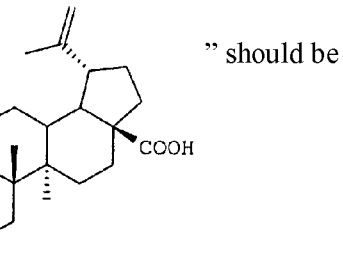 " should be

-- 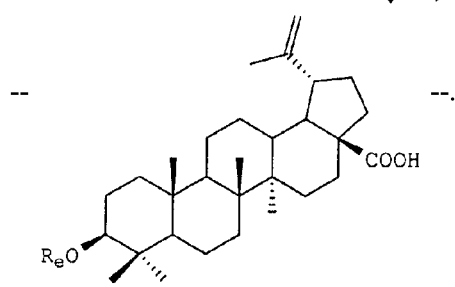 --.

At Column 33, line 60, " 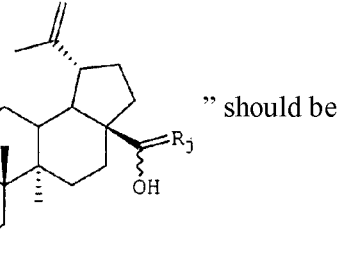 " should be

-- 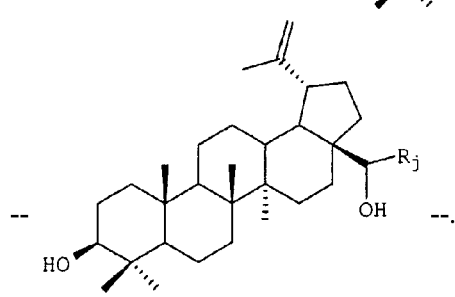 --.

UNITED STATES PATENT AND TRADEMARK OFFICE
CERTIFICATE OF CORRECTION

PATENT NO. : 7,414,042 B2  
APPLICATION NO. : 10/317361  
DATED : August 19, 2008  
INVENTOR(S) : John M. Pezzuto et al.

It is certified that error appears in the above-identified patent and that said Letters Patent is hereby corrected as shown below:

At Column 34, line 50, " 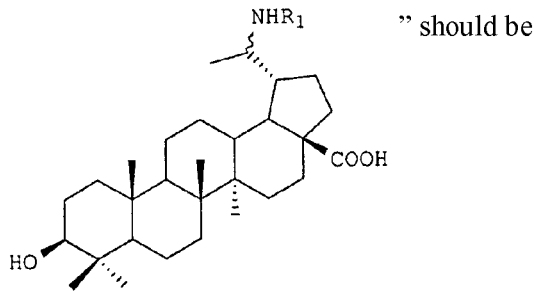 " should be

-- 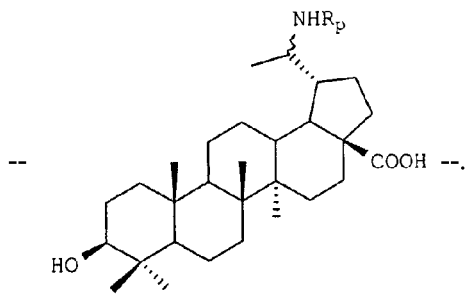 --.

Signed and Sealed this

Twenty-fourth Day of February, 2009

JOHN DOLL  
*Acting Director of the United States Patent and Trademark Office*